United States Patent
Lee et al.

(10) Patent No.: US 11,849,720 B2
(45) Date of Patent: Dec. 26, 2023

(54) ANTI-FREEZING COMPOSITION COMPRISING GOLD NANOPARTICLE WITH PEPTIDE

(71) Applicant: Korea University Research and Business Foundation, Seoul (KR)

(72) Inventors: Seungwoo Lee, Seoul (KR); Dong June Ahn, Seoul (KR); Dong Kwon Lim, Seoul (KR); Jae Won Lee, Seoul (KR); Sang Yup Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 808 days.

(21) Appl. No.: 16/702,059

(22) Filed: Dec. 3, 2019

(65) Prior Publication Data

US 2021/0106000 A1    Apr. 15, 2021

(30) Foreign Application Priority Data

Oct. 15, 2019  (KR) .................. 10-2019-0127972

(51) Int. Cl.
*A01N 1/02* (2006.01)
*A23L 3/37* (2006.01)
*C07K 19/00* (2006.01)
*C09K 3/18* (2006.01)
*B82Y 5/00* (2011.01)
*B82Y 40/00* (2011.01)

(52) U.S. Cl.
CPC ............ *A01N 1/0221* (2013.01); *A23L 3/37* (2013.01); *C07K 19/00* (2013.01); *C09K 3/18* (2013.01); *A23V 2002/00* (2013.01); *B82Y 5/00* (2013.01); *B82Y 40/00* (2013.01)

(58) Field of Classification Search
CPC .................................................. A01N 1/0221
See application file for complete search history.

(56) References Cited

FOREIGN PATENT DOCUMENTS

| | | |
|---|---|---|
| CN | 101918437 A | 12/2010 |
| EP | 2 565 200 A1 | 3/2013 |
| JP | 2011-504107 A | 2/2011 |
| KR | 10-2000-0029554 A | 5/2000 |
| KR | 10-2000-0029567 A | 5/2000 |
| KR | 10-2014-0049634 A | 4/2014 |
| KR | 10-2015-0108638 A | 9/2015 |
| KR | 1020180107887 A | 10/2018 |
| WO | 2015/080670 A1 | 6/2015 |
| WO | 2018/174325 A1 | 9/2018 |

OTHER PUBLICATIONS

Daniel E. Mitchell et al., Gold Nanoparticle Aggregation as a Probe of Antifreeze (Glyco) Protein-Inspired Ice Recrystallization Inhibition and identification of New IRI Active Macromolecules, Scientific Reports. (Year: 2015).*
Laura E. Wilkins et al., Site-specific conjugation of antifreeze proteins onto polymer-stabilized nanoparticles, Polymer Chemistry. (Year: 2019).*
Raoul Peltier, Biomimetic modification of crystal growth, Thesis. (Year: 2011).*
Peidong Yang et al. Shape Control of Colloidal Metal Nanocrystals, Small, 4, 310-315. (Year: 2008).*
Communication dated Jan. 26, 2021, issued by the Japanese Patent Office in application No. 2019-218787.
Lee et al., "Antifreezing Gold Colloids" JACS, 2019, vol. 141, pp. 18682-18693 (12 pages).
Hybrid multivalent antifreeze protein/polymer materials, 2018:1501639, 2018, 1 page.
The Extended European Search Report dated Feb. 24, 2021, issued by the European Patent Office in application No. 19213193.6.
Personick et al., "Making Sense of the Mayhem behind Shape Control in the Synthesis of Gold Nanoparticles", JACS, 2013, vol. 135, pp. 18238-18247 (10 pages).
Communication dated Oct. 11, 2021 from the China National Intellectual Property Administration in Chinese Application No. 201911306468.2.
Michelle L. Personick et al., "Making Sense of the Mayhem behind Shape Control in the Synthesis of Gold Nanoparticles", Journal of the American Chemical Society, 2013, vol. 135, pp. 18238-18247 (10 pages total).
Laura E. Wilkins et al., "Site-specific conjugation of antifreeze proteins onto polymer-stabilized nanoparticles", Royal Society of Chemistry, Polymer Chemistry, 2019, pp. 2986-2990 (5 pages total).
Grant of Patent issued Jan. 25, 2022 in Korean Application No. 10-2019-0127972.
Communication dated Sep. 23, 2021, from the Korean Intellectual Property Office in application No. 10-2019-0127972.

* cited by examiner

*Primary Examiner* — Michael G. Hartley
*Assistant Examiner* — Jagadishwar R Samala
(74) *Attorney, Agent, or Firm* — Sughrue Mion, PLLC

(57) ABSTRACT

The present invention provides a a nanostructure which includes: a core comprising one or more planes configured to come into planar contact with at least one plane of an ice crystal; and an oligopeptide which is conjugated to at least one plane of the core and comprises $(Thr)_n$-, $(Ala)_n$-, $(Ser)_n$-, or $(Gly)_n$-, wherein the nanostructure is a polyhedron-shaped nanostructure present in water in a colloidal form to control freezing, and n is an integer of 2 to 7.

18 Claims, 50 Drawing Sheets

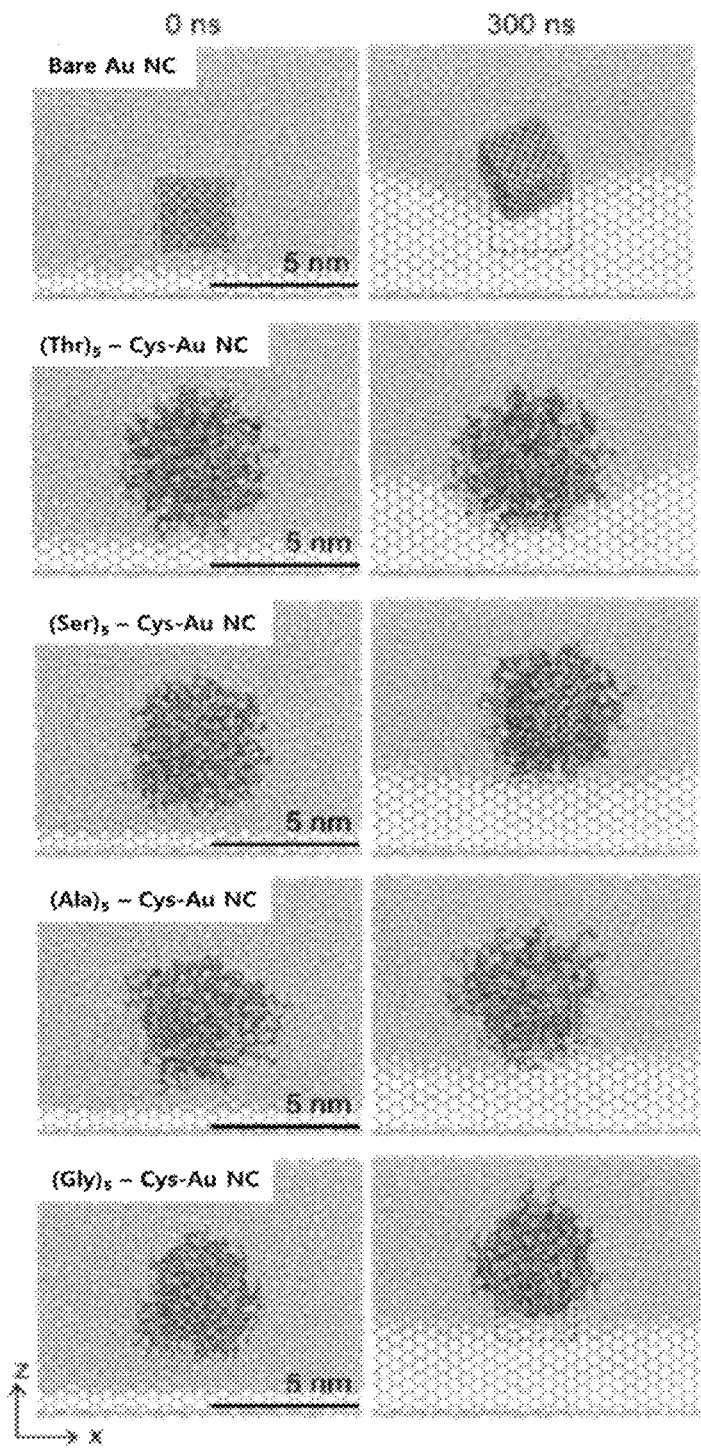

(Thr)$_2$-Cys-Au NC (full areal factor)

(Thr)$_5$-Cys-Au NC (half density)

(Thr)$_7$-Cys-Au NC (quarter density)

(Thr)$_2$-Cys-Au NC (full areal factor)

(Thr)$_5$-Cys-Au NC (full areal factor)

(Thr)$_7$-Cys-Au NC (full areal factor)

FIG. 19A

ANTI-FREEZING COMPOSITION COMPRISING GOLD NANOPARTICLE WITH PEPTIDE

BACKGROUND OF THE INVENTION

1. Field of the Invention

The present invention relates to an anti-freezing composition comprising gold nanoparticles with peptides attached thereto.

2. Description of the Related Art

Effects and capabilities of antifreeze protein (AFP) and antifreeze glycoprotein (AFGP) (hereinafter, collectively referred to as "AF(G)Ps") in inhibiting ice crystal growth have inspired persons having common knowledge in the technical field to which the present invention pertains to both understand and harness their mechanisms that exhibit antifreeze activities, thereby allowing those skilled in the art to use AF(G)Ps for a wide range of transformative applications. It is believed that regularly arranged AF(G)Ps with a specific sequence are adhered to facets of ice crystals, and consequently, micro- or nanocurvatures of the growing ice crystals, formed between regions in which the AF(G)Ps are anchored, make it more thermodynamically difficult for water molecules to crystallize.

Although a full rationalization of the underlying mechanism is yet to be addressed, two origins are likely to be involved in the ice adhesion of AF(G)Ps as follows. In the initial stage of study, a hydrogen-bonding was suggested as the most prevalent rationalization route towards this end. This is an intuitive explanation, because all amino acids have carbonyl and amine groups, the carbonyl and amine groups within the AF(G)Ps can widely form hydrogen bonds with water molecules. Artificial cryoprotectants such as poly(vinyl alcohol) (PVA) and graphene oxides (GOs) with a bunch of hydroxyl groups provide further evidence of the importance of hydrogen bonds in terms of ice crystal inhibition.

However, an approach depending only on hydrogen bonding have found to be inconsistent across the AF(G)Ps. (Sonnichsen, F. D.; DeLuca, C. I.; Davies, P. L.; Sykes, B. D. Refined solution structure of type III antifreeze protein: hydrophobic groups may be involved in the energetics of the protein-ice interaction. *Structure* 1996, 4, 1325-1337.; Chao, H.; Houston, M. E.; Hodges, R. S.; Kay, C. M.; Sykes, B. D.; Loewen, M. C.; Davies, P. L.; Sonnichsen, F. D. A diminished role for hydrogen bonds in antifreeze protein binding to ice. 1997 *Biochemistry*, 36, 14652-14660.; Zhang, W.; Laursen, R. A. Structure-function relationships in a type I antifreeze polypeptide the role of threonine methyl and hydroxyl groups in antifreeze activity. *J. Biol. Chem.* 1998, 273, 34806-34812.; Haymet, A. D. J.; Ward, L. G.; Harding, M. M. Winter flounder "antifreeze" proteins: synthesis and ice growth inhibition of analogues that probe the relative importance of hydrophobic and hydrogen-bonding interactions. *J. Am. Chem. Soc.* 1999, 121, 941-948.; Yang, C.; Sharp, K. A. Hydrophobic tendency of polar group hydration as a major force in type I antifreeze protein recognition. *Proteins* 2005, 59, 266-274.; Wierzbicki, A.; Dalal, P.; Cheatham III, T. E.; Knickelbein, J. E.; Haymet, A. D. J.; Madura, J. D. Antifreeze proteins at the ice/water interface: three calculated discriminating properties for orientation of type I proteins. *Biophys. J.* 2007, 93, 1442-1451.; Nutt, D. R.; Smith, J. C. Dual function of the hydration layer around an antifreeze protein revealed by atomistic molecular dynamics simulations. *J. Am. Chem. Soc.* 2008, 130, 13066-13073.; Smolin, N.; Daggett, V. Formation of ice-like water structure on the surface of an antifreeze protein. *J. Phys. Chem. B* 2008, 112, 6193-6202.; Mochizuki, K.; Molinero, V. Antifreeze Glycoproteins Bind Reversibly to Ice Via Hydrophobic Groups. *J. Am. Chem. Soc.* 2018, 140, 4803-4811.). For example, it empirically turns out that co-oligopeptides including threonine (Thr) and serine (Ser) exhibit more efficient inhibition of ice growth when a ratio of Thr to Ser is higher (Chao, H.; Houston, M. E.; Hodges, R. S.; Kay, C. M.; Sykes, B. D.; Loewen, M. C.; Davies, P. L.; Sonnichsen, F. D. A diminished role for hydrogen bonds in antifreeze protein binding to ice. 1997 *Biochemistry*, 36, 14652-14660.; Zhang, W.; Laursen, R. A. Structure-function relationships in a type I antifreeze polypeptide the role of threonine methyl and hydroxyl groups in antifreeze activity. *J. Biol. Chem.* 1998, 273, 34806-34812.). From the viewpoint of hydrogen bonding, this is counterintuitive because Thr is more hydrophobic than Ser. This result implies that the hydrophobicity of AF(G)Ps also contributes to their ice binding, and thereby resulting in the inhibition of ice growth. This importance of hydrophilic and hydrophobic dualities in the inhibition of ice growth has been confirmed during studies using amphipathic glycopolymers. As well as these empirical observations, numerical simulations for theoretically supporting the above discussions have been recently performed.

Another key factor for inhibiting ice growth is a facial organization of such amphiphilic moieties. Typically, the assembled AF(G)Ps form a flat array, which in turn facilitates interactions between ice and AF(G)Ps. In most of the artificial cryoprotectants developed so far, small or polymeric macromolecules have themselves been used without such planar organization. General advantages of these molecular cryoprotectants can be seen mainly in their diversity of chemical moieties being well suited for the purpose of ice growth inhibition and the versatile and cost effective potential to synthesize. The lack of appropriate micro/nanomaterials has also spurred the use of nongeometrically defined, molecular cryoprotectants, which in turn requires the use of cryoprotectant in a relatively high concentration to effectively inhibit ice growth.

Meanwhile, the synthesis and applications of gold (Au) colloidal nanoparticles (NPs) have undergone significant progress over the past two decades. With the advent of a variety of synthetic routes to produce Au NPs having highly uniform and different shapes, Au colloids have attracted a surge of interest from a myriad of fields such as biomedical therapy/sensors, plasmonics, optical metamaterials, optoelectronics, solar energy conversion, and many other applications. Many of these developments have primarily focused on taking advantage of Au colloidal plasmonic effects (i.e., localized surface plasmon resonance (LSPR)).

However, the abilities to precisely control both the shape and size of Au NPs may be used not only to modulate the LSPR effects but also to improve nanoscale interfacial interactions between ice and cryoprotectant molecular moieties.

PRIOR ART DOCUMENT

Patent Document

EP2565200A1

SUMMARY OF THE INVENTION

An object of the present invention is to provide a material capable of controlling freezing and/or a composition comprising the same.

In addition, another object of the present invention is to provide a composition for cryopreservation for increasing a survival rate of cells and a method thereof.

Further, another object of the present invention is to provide a composition for food cryopreservation, which can maintain a texture of food even when freezing and a method thereof.

1. A nanostructure including: a core comprising one or more planes configured to come into planar contact with at least one plane of an ice crystal; and an oligopeptide which is conjugated to at least one plane of the core and comprises $(Thr)_n$-, $(Ala)_n$-, $(Ser)_n$-, or $(Gly)_n$-, wherein the nanostructure is a polyhedron-shaped nanostructure present in water in a colloidal form to control freezing, and n is an integer of 2 to 7.
2. The nanostructure according to the above 1, wherein the core has a shape of tetrahedron, truncated tetrahedron, hexahedron, truncated hexahedron, octahedron, truncated octahedron, decahedron, dodecahedron, icosahedron, tetrakishexahedron, hexakisoctahedron, or rhombic dodecahedron.
3. The nanostructure according to the above 1, wherein the core is made of gold (Au), silver (Ag), platinum (Pt), palladium (Pd), aluminum (Al), copper (Cu), iron oxide ($Fe_3O_4$), or silicon dioxide ($SiO_2$), or an alloy including at least two thereof.
4. The nanostructure according to the above 1, wherein the core is made of gold (Au), platinum (Pt), iron (Fe), iron oxide ($Fe_3O_4$), silicon (Si), or silicon dioxide ($SiO_2$), or an alloy including at least two thereof.
5. The nanostructure according to the above 1, wherein n is 3 to 6.
6. The nanostructure according to the above 1, wherein the oligopeptide comprises $(Thr)_n$-, or $(Ala)_n$-.
7. The nanostructure according to the above 1, wherein the core has a diameter of 50 nm to 100 nm.
8. The nanostructure according to the above 1, wherein 0.07 to 0.25 oligopeptides per $nm^2$ are attached to the plane.
9. The nanostructure according to the above 1, wherein the core has a shape of a hexahedron or octahedron.
10. The nanostructure according to the above 1, wherein the core is made of gold (Au).
11. The nanostructure according to the above 1, wherein n is 5.
12. The nanostructure according to the above 1, wherein 0.1 to 0.2 oligopeptides per $nm^2$ are attached to the plane.
13. The nanostructure according to the above 1, wherein the freezing control is performed by inhibiting recrystallization of the ice.
14. A composition for controlling freezing comprising the nanostructure according to any one of above 1 to 13.
15. A composition for freezing a cell comprising the nanostructure according to any one of above 1 to 13.
16. A composition for freezing a food comprising the nanostructure according to any one of above 1 to 13.
17. A method for controlling freezing including: preparing a nanostructure comprising: a core comprising one or more planes configured to come into planar contact with at least one plane of an ice crystal; and an oligopeptide which is conjugated to at least one plane of the core and comprises $(Thr)_n$-, $(Ala)_n$-, $(Ser)_n$-, or $(Gly)_n$-, wherein the nanostructure is a polyhedron-shaped nanostructure present in water in a colloidal form to control freezing, and n is an integer of 2 to 7; and adding the prepared nanostructure to a solvent.
18. A method for cryopreserving a cell including: preparing a nanostructure comprising: a core comprising one or more planes configured to come into planar contact with at least one plane of an ice crystal; and an oligopeptide which is conjugated to at least one plane of the core and comprises $(Thr)_n$-, $(Ala)_n$-, $(Ser)_n$-, or $(Gly)_n$-, wherein the nanostructure is a polyhedron-shaped nanostructure present in water in a colloidal form to control freezing, and n is an integer of 2 to 7; and adding the prepared nanostructure to a solution containing the cells.
19. A method for cryopreserving a food including: preparing a nanostructure comprising: a core comprising one or more planes configured to come into planar contact with at least one plane of an ice crystal; and an oligopeptide which is conjugated to at least one plane of the core and comprises $(Thr)_n$-, $(Ala)_n$-, $(Ser)_n$-, or $(Gly)_n$-, wherein the nanostructure is a polyhedron-shaped nanostructure present in water in a colloidal form to control freezing, and n is an integer of 2 to 7; and adding the prepared nanostructure to the food for treatment.

By using the material and/or composition comprising the same according to the invention, it is possible to inhibit a recrystallization of ice and control the freezing. Thereby, the survival rate of cells may be increased during cell cryopreservation, and the texture of food may be maintained even when freezing.

BRIEF DESCRIPTION OF THE DRAWINGS

The above and other objects, features and other advantages of the present invention will be more clearly understood from the following detailed description taken in conjunction with the accompanying drawings, in which:

FIG. 16A is time-lapse photographs taken to show simulated ice growth for bare Au NC ($1^{st}$ row), and oligopeptide-conjugated Au NCs ($2^{nd}$ to $5^{th}$ rows)

FIG. 19A is a diagram showing a modulation of interfacial contact between water and ice according to shapes of the Au colloids.

DETAILED DESCRIPTION OF THE INVENTION

Figure 1A:
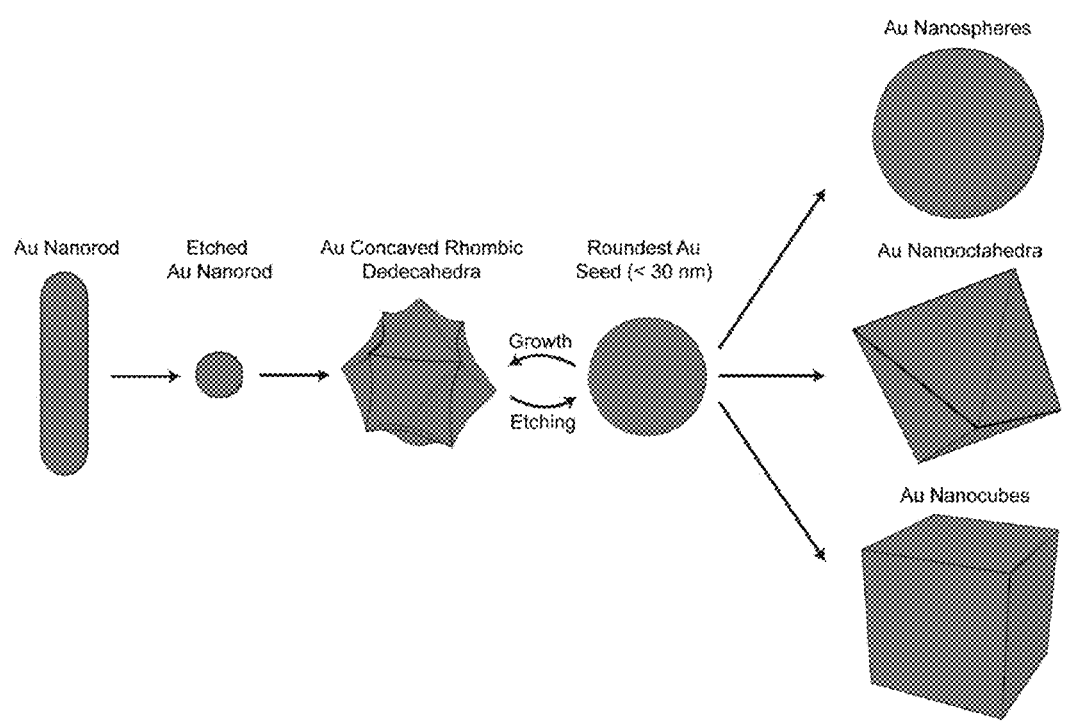
FIG. 1A is views showing synthesis processes of Au colloids, and views FIG. 1B showing results of confirming distributions according to a length L and an aspect ratio of Au nanoparticles (NPs) prepared by a method according to an embodiment of the present invention.

Hereinafter, the present invention will be described in more detail with reference to the accompanying drawings. However, some embodiment of the present invention, but not limited thereto, are illustrated. In fact, these invention may be practically embodied in various formed and should not be construed to limit the present invention to the embodiments proposed in the present disclosure. Singular forms used in the specification and appended claims may also include plural forms unless otherwise specifically indicated.

As used herein, the term "hermal hysteresis" refers to a phenomenon in which a freezing temperature and a melting temperature differently occur. If a nucleating agent is present in water, the freezing temperature and the melting temperature are substantially the same as each other. However, if no nucleating agent is present or the nucleating agent is an antifreeze protein, the freezing temperature occurs below the melting temperature.

As used herein, the term "ice recrystallization" refers to a process of growing from small ice crystals to larger ice crystals, and the term "Ostwald ripening" refers to such a recrystallization that occurs due to a pressure differential occurring in relation to a difference in energy of the surrounding environment and the surface energy of crystals, which may be performed in a dissolution-diffusion-refreezing or a sublimation-diffusion-condensation mechanism.

In cryopreservation, cell membranes may be damaged due to ice recrystallization during melting, thereby resulting in damaging cells and tissues due to occurred cell dehydration. Since organisms living in a lower-temperature environment may be more easily damaged by ice recrystallization, AFP or AFGP have been developed. Because the AF(G)Ps are adhered to surfaces of ice to inhibit the ice from growing, they have been utilized as an additive in fields where ice recrystallization causes a problem. The inventors of the present invention have developed a material for controlling freezing using a peptide derived from AF(G)Ps, and have completed the present invention by proving that the spatial arrangement of AF(G)P-derived peptides greatly influences the anti-freezing effects.

In the present disclosure, "antifreeze protein" and "anti-freeze protein" or "AFP" may be used interchangeably, and "antifreeze glycoprotein" and "anti-freeze glycoprotein" or "AFGP" may be used interchangeably. AFP and AFGP are collectively referred to as "AF(G)Ps." The AF(G)Ps are found in a variety of animals, plants, fungi and bacteria, and they are known to conjugate to ice crystals to inhibit growth and recrystallization of ice. These properties of AF(G)P have been used to preserve biological samples at a low temperature. According to recent studies, the AF(G)Ps have a special type of tertiary structure for conjugating to ice according to their types, and it is known that a large number of Thrs are present in a direction contacting with ice, and Alas are present in an auxiliary manner.

In the present disclosure, the terms "antifreezing," "anti-freezing," "freezing control," "freeze control," "freezing suppression" and "freeze suppression" are used interchangeably, and refer to actions of lowering a freezing point, preventing ice formation or lowering a speed of ice formation, preventing ice recrystallization, lowering a speed of ice recrystallization, or maintaining a size of ice crystals to be small.

As used herein, the term "colloid" refers to a mixture or a dispersed material, in which microscopically dispersed soluble particles or insoluble particles are suspended in other materials. Unlike solutions in which a solvent and a solute have one phase, the colloid has a dispersed phase and a continuous phase.

In the present disclosure, the terms "oligopeptide," "polypeptide," "peptide" and "protein" are used interchangeably and refer to polymeric compounds including amino acid residues covalently bonded through peptide bonding. In the present invention, peptides synthesized through techniques known in the art may be used. A method for synthesizing the peptide may be a chemical method or a biological method, wherein the chemical method may be, for example, a solution phase method; solid phase methods including tert-butyloxycarbonyl (Boc)/benzyl (Bzl) strategy and 9-fluorenylmethoxycarbonyl (Fmoc)/tert-butyl (t-Bu) strategy (Kent SBH, Mitchell AR, Engelhard M, Merrifield RB (1979) Mechanisms and prevention of trifluoroacetylation in solid-phase peptide synthesis. Proc Natl Acad Sci USA 76(5): 2180-2184); a method for immobilizing a first amino acid to a resin and extending peptide chains in order of sequences; or a method using a microwave, and the biological method may be a method using microorganisms, but it is not limited thereto.

In the present disclosure, the term "planar contact" and "plane or facet contact" is used interchangeably, and means a case in which, when contacting a surface with another surface, a plane is substantially formed at a boundary therebetween, and is used separately from the cases of a line contact, a point contact, or a curved surface contact where a curved surface is formed at the boundary. A nanostructure of the present invention has one or more planes which can come into planar contact with ice crystal planes, and the corresponding plane has a hydrophobic functional group or a hydrophilic functional group, or otherwise, and has an amino acid residue having hydrophobic or hydrophilic functional groups exposed therefrom. The polyhedron capable of planar contacting may be a tetrahedron, truncated tetrahedron, hexahedron, truncated hexahedron, octahedron, truncated octahedron, decahedron, dodecahedron, icosahedron, tetrakishexahedron, hexakisoctahedron, or rhombic dodecahedron, but it is not limited thereto. In one embodiment of the invention, the polyhedron is the hexahedron or octahedron.

Figure 1B:
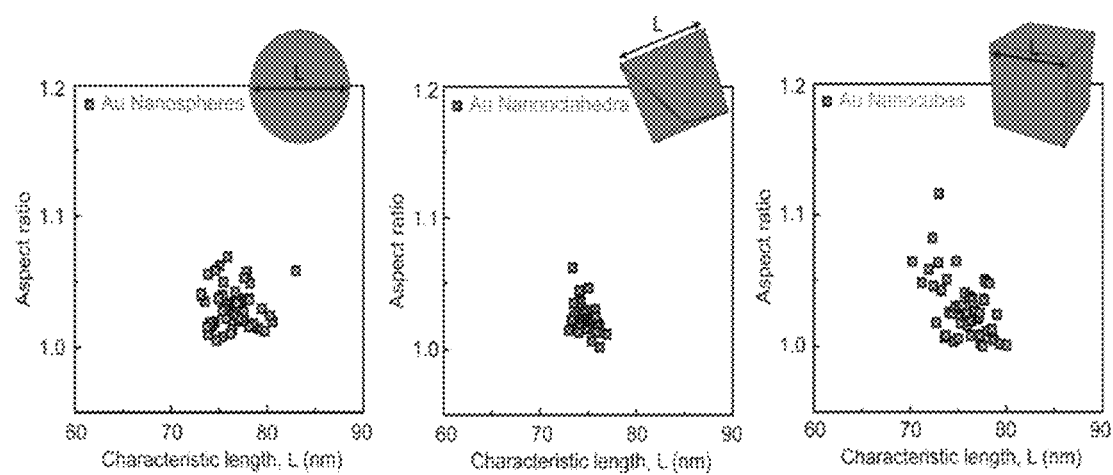
FIG. 1C is views showing different shapes of Au NPs, a tetrahedron, a truncated tetrahedron, a hexahedron, a truncated hexahedron, an octahedron, and a truncated octahedron (from left to right)

As used herein, the term "truncated polyhedron" refers to a polyhedron which is one of the Archimedes polyhedrons and is made by truncating vertices of the polyhedron (FIG. 1B).

As used herein, the term "core" refers to a portion forming a basic skeleton of the nanostructure. The core may use elements which are nontoxic, substantially nontoxic, or less toxic to the cell or body. In one embodiment of the present invention, the core may be made of, for example, gold (Au), silver (Ag), platinum (Pt), palladium (Pd), aluminum (Al), copper (Cu), iron oxide ($Fe_3O_4$), or silicon dioxide ($SiO_2$), or an alloy including at least two thereof, and in another embodiment of the present invention, the core may be made of gold (Au), platinum (Pt), iron (Fe), iron oxide ($Fe_3O_4$), silicon (Si), or dioxide silicon ($SiO_2$), or an alloy including at least two thereof, but it is not limited thereto. In another embodiment of the invention, the core is made of gold (Au).

In one embodiment of the present invention, the core has a diameter of 150 nm or less, 10 nm to 140 nm, 20 nm to 130 nm, 30 nm to 120 nm, 40 nm to 110 nm, 50 nm to 100 nm, 60 nm to 90 nm, or 75 nm, however, the diameter thereof is not limited to the above-described range so long as the nanostructures according to the invention can be suspended in a solution in a colloidal form. The diameter of the core may be adjusted so as to have colloidal properties in consideration of the material, density, shape, and the like of the used core by those skilled in the art. However, when the diameter of the core is less than 10 nm, the freezing control effect may not occur.

As used herein, the term "diameter" refers to the shortest distance between the planes facing from the polyhedron, and when the nanostructure is spherical, it means twice the radius.

The nanostructure according to the invention includes a core and oligopeptides conjugated to the core. The oligopeptide may be an amino acid having a hydrophobic functional group, for example His, Gly, Pro, Ala, Val, Ile, Leu, or Met, and may be an amino acid having a hydrophilic functional group, for example Arg, Ser, Thr, Tyr, Cys, Asp, or Glu, and may be an amino acid having hydrophobic and hydrophilic functional groups such as Thr.

In one embodiment of the invention, the oligopeptide conjugated to the core may include one or more amino acids selected from the group consisting of $(Thr)_n$, $(Ala)_n$, $(Gly)_n$ and $(Ser)_n$, and in another embodiment, the oligopeptide is $(Thr)_n$ or $(Ala)_n$: wherein n is an integer of 1 to 8, an integer of 2 to 7, an integer of 3 to 6, or 5, but it is not limited thereto. Unless otherwise defined, in the present disclosure, the oligopeptide describes sequences from an N terminus to C terminus. For example, $(Thr)_5$- means (N-terminus) Thr- Thr-Thr-Thr-Thr-(C-terminus), and means one conjugated to the nanostructure of the present invention directly or through an additional amino acid linked to the C terminus.

In another embodiment of the present invention, the oligopeptide was prepared of $(Thr)_5$-conjugated Au nanoparticles (NPs) using structural properties of AF(G)Ps, and in addition, in order to confirm the role of a hydrophilic or hydrophobic functional group, Au NPs with $(Ser)_5$ in which —$CH_3$ is replaced by H in Thr, $(Ala)_5$ in which —OH is replaced by H in Thr, and $(Gly)_5$ in which both —$CH_3$ and —OH are replaced by H in Thr were prepared, respectively. In particular, Cys may be further included at the C-terminus to conjugate the oligopeptide to the core, but in addition, a configuration for conjugating the oligopeptide to the core surface, which is known in the art, may be added.

In one embodiment of the present invention, the oligopeptides conjugated to the core may be attached in a maximum of 0.07 to 0.25, 0.075 to 0.23, 0.1 to 0.2, or 0.13 to 0.17 per $nm^2$, but the number of conjugated oligopeptides may vary depending on properties of the oligopeptide, such as a length or sequence of the oligopeptide. The conjugating force with the ice interface is correlated to the number of oligopeptides conjugated per unit area, and the number of functional groups (hydrophobic and hydrophilic groups) that can interact with water.

The present inventors has confirmed that the nanostructure of the present invention has an effect of inhibiting ice recrystallization higher than the sphere-shaped nanostructures having substantially the same diameter. In addition, the inventive nanostructure has an effect so that the ice is formed in a shape whose end is blunt, and not a jagged or needle-like shape.

If the ice crystals have the jagged or needle-like shape, when freezing and storing the cells or foods, cell membranes and/or cell walls are destroyed, thereby resulting in a decrease in the survival rate of the cells and a deterioration in texture of the food. However, when adding the composition including the nanostructure according to the present invention, the ice formed as described above is grown without direction, thereby increasing the survival rate of a cell during cryopreservation of the cell, and maintains the texture of the food during cryopreservation. Therefore, due to these advantages, the nanostructure according to the present invention may be used not only as a raw material for common freezing control but also may be suitably used in freezing the cells and foods.

In one embodiment of the present invention, the composition for controlling freezing according to the present invention includes a nanostructure including: a core which includes at least one plane configured to come into planar contact with at least one plane of a ice crystal, and has a shape of tetrahedron, truncated tetrahedron, hexahedron, truncated hexahedron, octahedron, truncated octahedron, decahedron, dodecahedron, icosahedron, tetrakishexahedron, hexakisoctahedron, or rhombic dodecahedron; and an oligopeptide which is conjugated to one or more planes of the core and includes $(Thr)_n$-, $(Ala)_n$-, $(Ser)_n$-, or $(Gly)_n$-. In another embodiment of the present invention, the core included in the nanostructure of the composition for controlling freezing according to the present invention has two or more shapes selected from the group consisting of tetrahedron, truncated tetrahedron, hexahedron, truncated hexahedron, octahedron, truncated octahedron, decahedron, dodecahedron, icosahedron, tetrakishexahedron, hexakisoctahedron, and rhombic dodecahedron.

In one embodiment of the present invention, cells that can be cryopreserved using a cell cryopreservation composition according to the present invention may include prokaryotic cells; eukaryotic cells; microorganisms; animal cells; cancer cells, sperms; eggs; stem cells including adult stem cells, embryonic stem cells, and dedifferentiated stem cells; blood cells including cord blood, white blood cells, red blood cells, and platelets; and tissue cells including kidney cells, liver cells, and muscle cells, but it is not limited thereto.

In one embodiment of the present invention, there are provided a method for controlling freezing including: preparing the nanostructure according to the present invention; and adding the prepared nanostructure to a solvent, a method for cryopreserving cells including: preparing the nanostructure according to the present invention; and adding the prepared nanostructure to a solution containing cells, and a method for cryopreserving a food including: preparing the nanostructure according to the present invention; and adding the prepared nanostructure to the food for treatment.

When numerical values are described using a range in the present disclosure, it is considered that all numerical values within the corresponding range are disclosed in the present invention.

Those skilled in the art will understand the case in which "about" should be used unavoidably, and the term "about" as used herein will be understood to include numerical values within a margin of error.

The term "substantially the same" as used herein means a case in which there is a difference in the same or unrecognized degree within the margin of error. As used herein, the term "substantially free," "be substantially free" or similar expressions thereto refer to a case of zero or zero is included within the margin of error, or a case of negligible for those skilled in the art to recognize.

EXAMPLE

Example 1. Methods 1.1 Synthesis of Au Colloids.

Figure 1C:
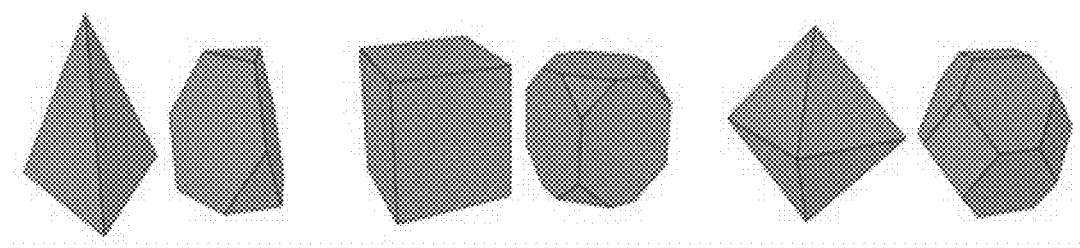

Au colloids (Au nanospheres (NSs), Au nanocubes (NCs), and Au nanooctahedra (NOs)) were synthesized by a seed-mediated method in conjunction with a selective etching of the vertices/edges. First, the Au nanorods (NRs) were synthesized using a silver-assisted method (FIG. 1). Au seeds for Au NRs were synthesized by injecting 300 μL of 10 mM sodium borohydride into an aqueous solution containing 125 μL of 10 mM $HAuCl_4$ and 5 mL of 100 mM hexadecyltrimethylammonium bromide (CTAB). Then, the Au NRs were grown by adding 200 mL of 100 mM CTAB, 10 mL of 10 mM $HAuCl_4$, 1.8 mL of 10 mM silver nitrate, 1.14 mL of 100 mM L-ascorbic acid, and 240 μL of a seed solution in succession. After mild stirring for 1 minute, the solution was left for 2 hours.

To obtain highly uniform NS seeds, both ends of the Au NR were selectively etched out by injecting 60 μM of $HAuCl_4$ into a 50 mM of CTAB aqueous solution containing Au NRs in 2 optical density (OD) concentrations. After mild stirring at 40° C. for 4 hours, the etched Au NRs were resuspended in a 100 mM of cetylpyridinium chloride (CPC) aqueous solution. These etched Au NRs were grown into concave rhombic dodecahedra (CRD) by mixing 20 mL of 10 mM CPC, 350 μL of 10 mM $HAuCl_4$, 4.5 mL of 100 mM ascorbic acid, and 1 mL of etched Au NRs in 1 OD concentration, and were etched into NS seeds by mixing with a 60 μM of $HAuCl_4$ aqueous solution under mild stirring at 40° C. for 4 hours. The CRD growth and subsequent etching of the vertices/edges were repeated 2 times using 5 mL of etched CRD as seeds to refine the uniformity of the NS seeds.

These NS seeds were used to produce Au NSs, Au NCs, and Au NOs. To obtain Au NSs, the above-mentioned CRD growth and etching method was followed using 2 mL of etched CRD as seeds. For the synthesis of Au NCs, 5 mL of 100 mM CPC, 500 µL of 100 mM KBr, 100 µL of 10 mM HAuCl$_4$, 150 µL of 100 mM ascorbic acid, and 500 µL of NS seeds in 1 OD concentration were mixed and allowed to react for 1 hour. The Au NOs were generated by adding 100 µL of 10 mM HAuCl$_4$, 13 µL of 100 mM ascorbic acid, and 500 µL of NS seeds in 1 OD concentration into an aqueous solution containing 5 mL of 100 mM CPC under mild stirring for 1 hour.

1.2 Conjugation of Oligopeptides to Au Colloids.

To conjugate the Au colloids with the antifreezing oligopeptides, pseudo-covalent bonding of C-terminal cysteine (Cys) was utilized. Briefly, the Au colloids synthesized as described above and suspended in deionized (DI) water were mixed with an excess amount of oligopeptides and incubated for 30 min to ensure full coverage. After the incubation, the excess amount of oligopeptides were removed three times through centrifugation and resuspended in 0.01% by weight ('wt. %') of sodium dodecyl sulfate (SDS) in water.

1.3 Numerical Simulation of Au Colloidal Scattering.

Figure 3A:
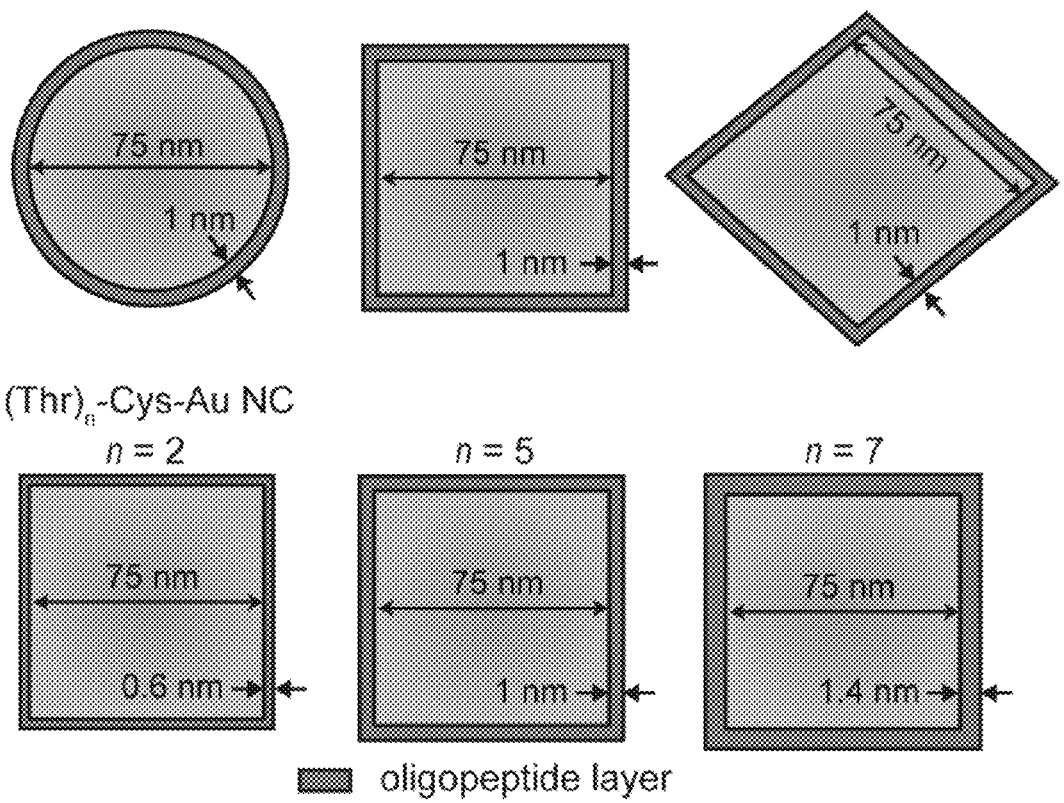
FIG. 3A is views showing a simulation model in which 2 mer, 5 mer and 7 mer oligopeptides are set to be 0.60 nm, 1.00 nm and 1.40 nm, respectively, and views FIG. 3B to FIG. 3D showing absorption spectra of bare Au colloids and oligopeptide-conjugated Au colloids.
Figure 3B:
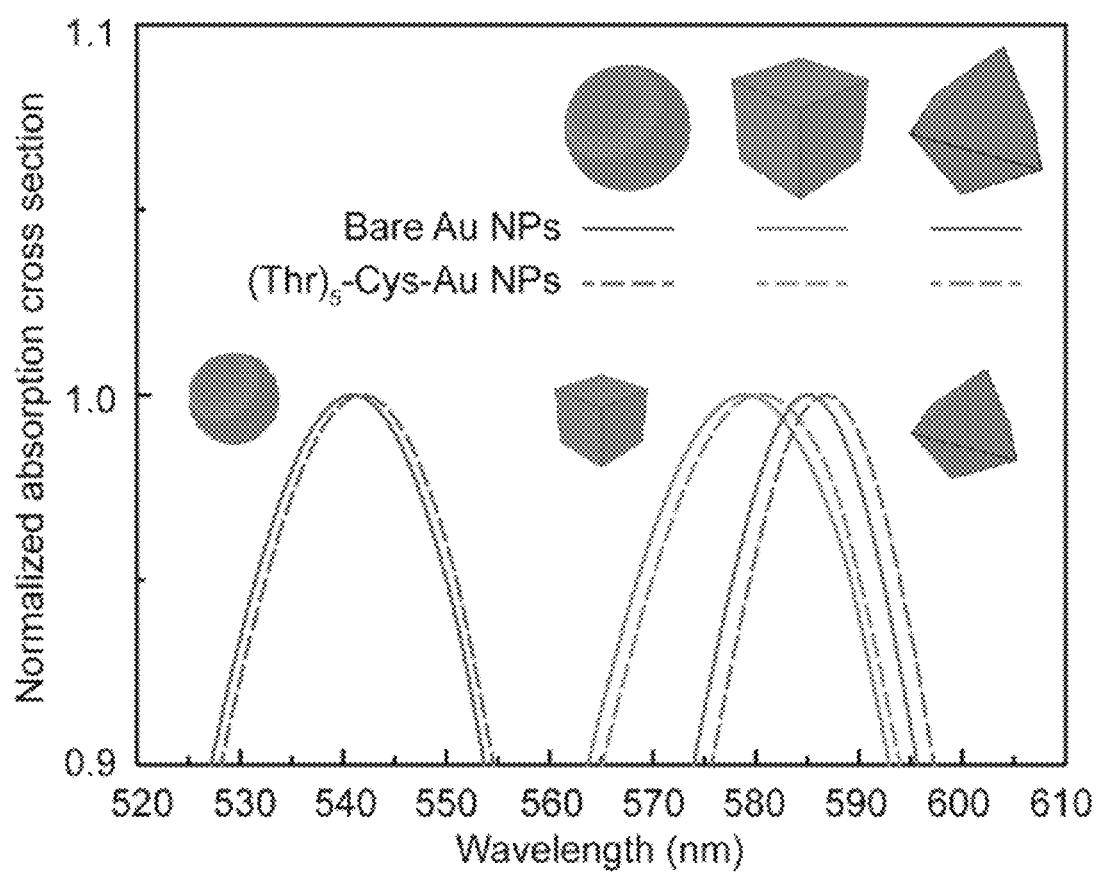
Figure 3C:
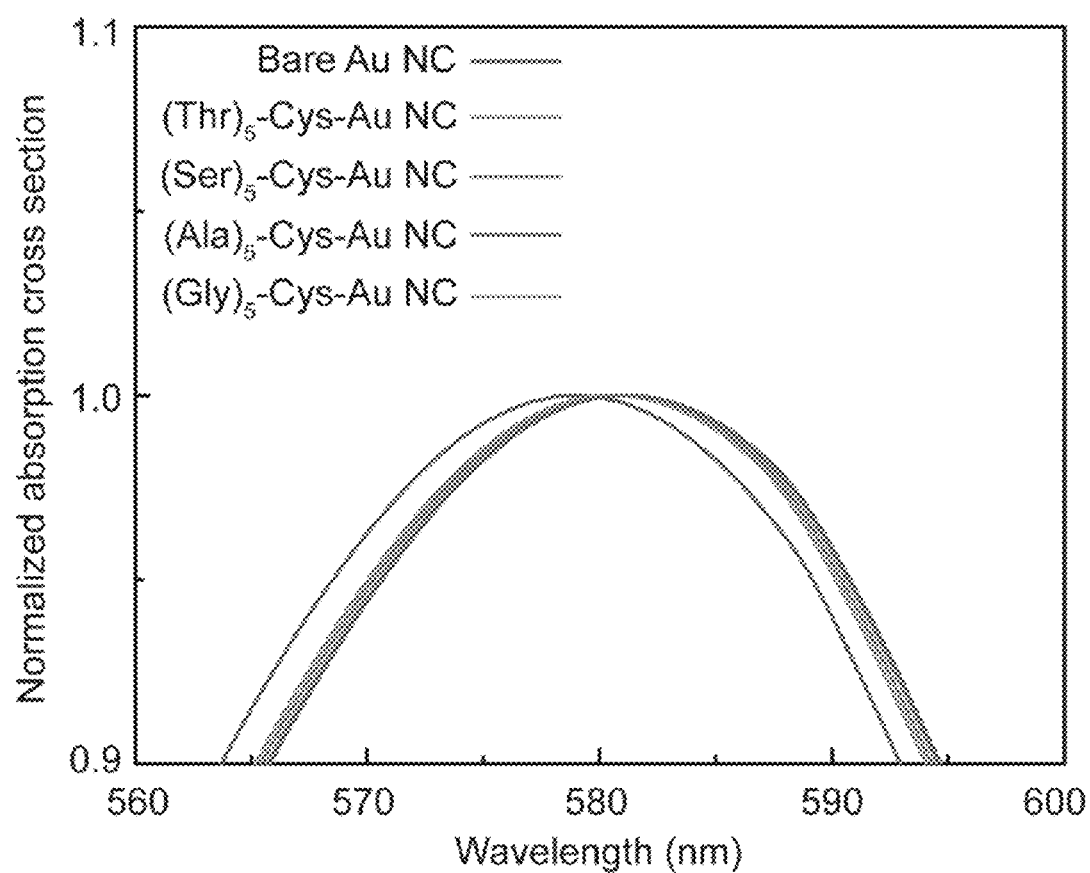

To theoretically predict the scattering behavior of Au colloids, finite-difference time-domain (FDTD), supported by a commercial software package (2014 CST Microwave Studio), was used. A dielectric constant of Au was based on the Johnson, P. B.; Christy, R. W. Optical constants of the noble metals. Phys. Rev. B 1972, 6 (12), 4370-4379; a thickness of the oligopeptides was varied from 0.60 nm to 1.40 nm, according to monomer numbers (n). These thicknesses were determined according to conformations of oligopeptides, which were calculated by all atom (AA) molecular dynamics (MD) simulation. To reflect the DF microscopy spectral analysis (FIG. 11), scattering cross-section (nm$^2$) spectra of the Au colloids were numerically calculated. Absorption cross-section (nm$^2$) spectra of the bare Au colloids or oligopeptide-conjugated Au colloids were calculated for the rationalization of the UV-Vis absorption spectra shown in FIGS. 3b to d.

To theoretically quantify effects of oligopeptide thickness on the Au colloid's UV-Vis absorption spectra, a shift of the localized surface plasmon resonance (LSPR) extinction peak were numerically simulated as a function of refractive index of oligopeptide layers with different thicknesses from each other. Then, the refractive index, used for such a numerical simulation, were correlated with oligopeptide density using effective medium theory (Maxwell-Garnett approximation) as given by the following equation:

$$\left(\frac{\varepsilon_{\mathit{eff}} - \varepsilon_h}{\varepsilon_{\mathit{eff}} + 2\varepsilon_h}\right) = \delta_i \left(\frac{\varepsilon_i - \varepsilon_h}{\varepsilon_i + 2\varepsilon_h}\right)$$

wherein, $\varepsilon_{\mathit{eff}}$, $\varepsilon_i$, $\varepsilon_h$, and $\delta i$ denote an effective dielectric constant of the medium, an effective dielectric constant of inclusions, an effective dielectric constant of a host, and a volume fraction of the inclusions, respectively. The inclusion and host medium were set as the oligopeptides and water ($\varepsilon_h$=1.33), respectively. The dielectric constant for oligopeptide was obtained from McMeekin, T. L.; Groves, M. L.; Hipp, N. J. Refractive indices of amino acids, proteins, and related substances; American Chemical Society: Washington, D C, 1964.

1.4 Quantification of Oligopeptides Attached onto Au Colloids.

To experimentally quantify an amount of the oligopeptides attached onto Au colloids, the oligopeptides were subjected to the reductive detachment by NaBH$_4$, and thiol-selective detector mediated fluorometric assay (Lee, H. E.; Ahn, H. Y.; Mun, J.; Lee, Y. Y.; Kim, M.; Cho, N. H.; Chang, K.; Kim, W. S.; Rho, J.; Nam, K. T. Amino-acid- and peptide-directed synthesis of chiral plasmonic gold nanoparticles. Nature 2018, 556 (7701), 360-365.) was carried out. Frist, the oligopeptide-conjugated Au colloids were centrifuged three times and resuspended in 0.01 wt. % of sodium dodecyl sulfate (SDS) to thoroughly remove the non-conjugated oligopeptides. To detach the oligopeptides from the Au colloids, 25 uL of 100 mM NaBH$_4$ was added to 75 uL of the oligopeptide-conjugated Au colloids. After the incubation for 5 min at room temperature, the solution was centrifuged again to separate Au colloids from the released oligopeptides. Aliquot of supernatant containing freely dispersed oligopeptide was further incubated overnight to deactivate the remaining NaBH$_4$.

Figure 4A:
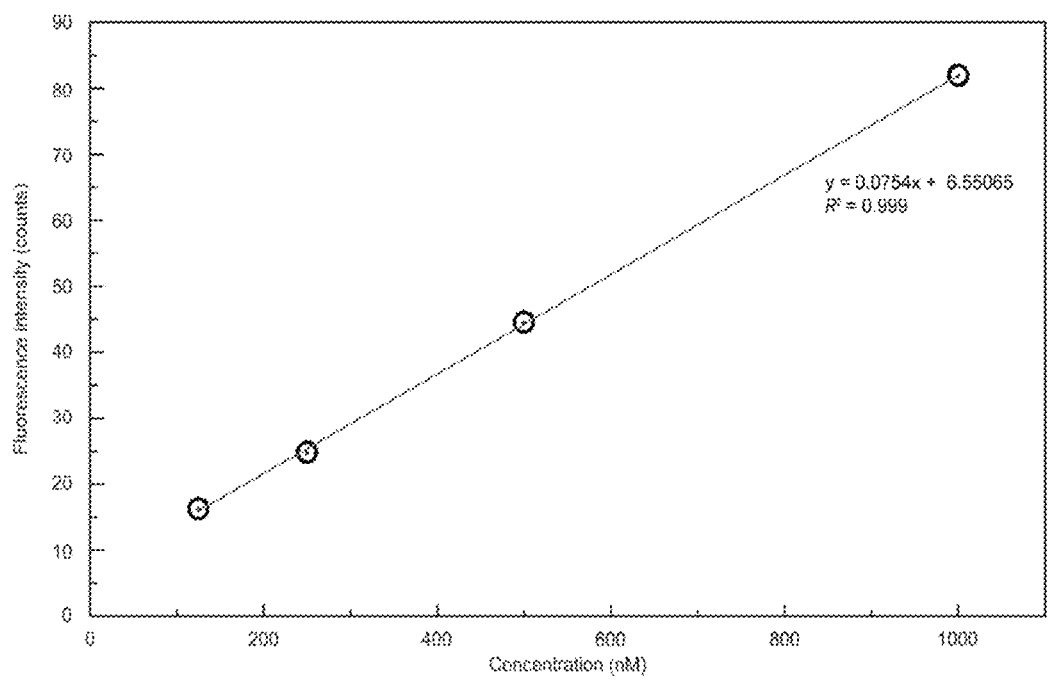
FIG. 4A is a graph showing a standard concentration curve for fluorescence quantification of oligopeptides.
Figure 4B:
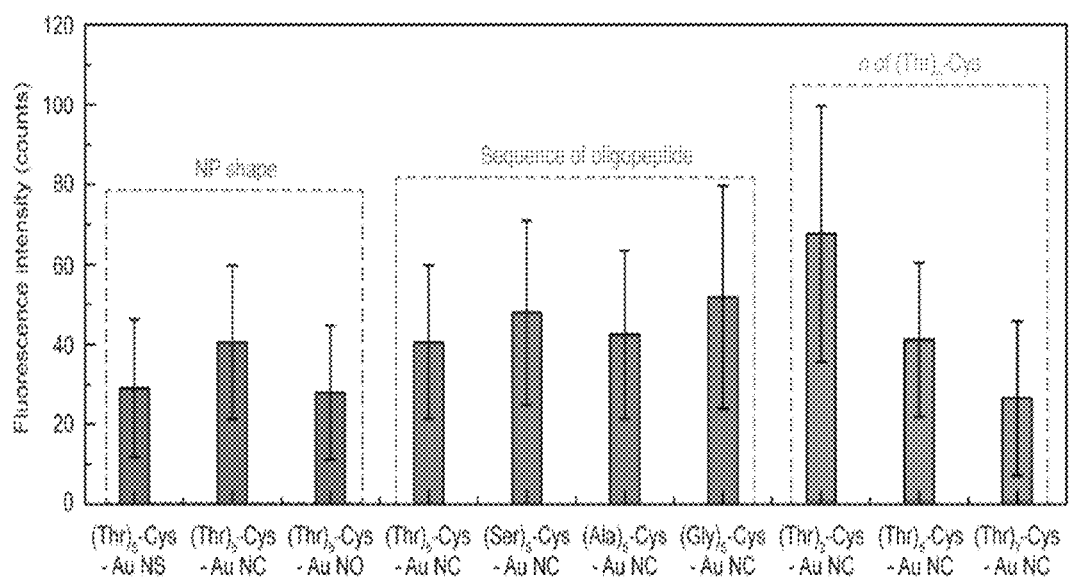
FIG. 4B is graphs showing fluorescence intensities obtained from the detached oligopeptides.

The detached oligopeptides were quantified by using a thiol detective fluorometric detector (thiol detection assay kit, Cayman Chemical, 700340). The oligopeptides were mixed with the thiol detective fluorometric detector in a ratio of 1:1 in the presence of thiol assay buffer (100 mM Potassium Phosphate, 1 mM EDTA, pH 7.4). Then, the solution was incubated at room temperature for 5 min, thereby allowing the detector to react with a thiol group so as to emit a fluorescent signal. The fluorescence was monitored at an excitation wavelength of 380 nm and an emission wavelength of 480 to 520 nm. Finally, the concentrations of the detached oligopeptides were calculated from the measured fluorescence intensity using the standard curve as a reference (FIG. 4).

1.5 Characterization of Ice Recrystallization Inhibition (IRI).

For IRI activity analysis, both splat and sucrose sandwich assays were simultaneously performed to determine an extent of ice recrystallization (Mitchell, D. E.; Clarkson, G.; Fox, D. J.; Vipond, R. A.; Scott, P.; Gibson, M. I. Antifreeze protein mimetic metallohelices with potent ice recrystallization inhibition activity. J. Am. Chem. Soc. 2017, 139 (29), 9835-9838.; (9) Budke, C.; Heggemann, C.; Koch, M.; Sewald, N.; Koop, T. Ice recrystallization kinetics in the presence of synthetic antifreeze glycoprotein analogues using the framework of LSW theory. J. Phys. Chem. B 2009, 113 (9), 2865-2873.). Herein, the oligopeptide-conjugated Au colloids were centrifuged and resuspended in DI water to thoroughly eliminate side effects from the remaining organic ligands before the characterization. To test the IRI activity using the splat assay, a 10 µL sample was dropped from a height of 1.5 m onto a surface of a glass coverslip precooled to −70° C. so as to form a thin film of ice. The glass coverslip with the ice thin film was transferred onto a Peltier cooler set at −20° C. Then, the temperature of the glass coverslip was gradually increased to −6° C. at a rate of 5° C./min, and the sample was annealed at the corresponding temperature. During recrystallization of ice for 30 min, dark-field optical microscopy (DFOM) images were taken. These DFOM images were quantified by using a code that was developed in-house to verify a grain size of the recrystallized ice. Ten of the largest ice crystal domains in the field of view were chosen and a mean diameter thereof was obtained to evaluate the IRI activity. A mean largest grain size (MLGS) was calculated using the averaged results from three individual experiments from each sample.

To characterize the IRI activity using the sucrose sandwich assay, the samples were sandwiched between two coverslips in the presence of 45 wt. % of sucrose, and placed on the Peltier cooler. After freezing the samples to −50° C., the temperature of the Peltier cooler was increased to −8° C. at a rate of 10° C./min. Then, the samples were annealed at the corresponding temperature for 30 min. To evaluate the IRI activity, DFOM images were taken every 5 min and radii of ice crystals were measured using the in-house developed code. The cube of time-traced mean ice crystal radius was calculated to quantify the IRI activity. Three individual experiments were carried out and a mean value was deduced from the results.

1.6 Directional Growth of Single Crystalline Ice.

First, a glass microfluidic channel was developed by taping a double-sided adhesive tape on a slide glass and placing a cover glass on a top thereof. Then, DI water was injected into this channel and then sealed with transparent nail polish. To induce a spatial temperature (T) gradient, one end of the channel was placed on the Peltier cooler at −° C., while the other end thereof remained at room temperature (15 to 20° C.) condition. Under this condition, a single crystalline ice-water interface was formed at somewhere between the Peltier cooler and ambient temperature area.

1.7 Sucrose Assisted Dynamics Ice Shaping (DIS) Assay.

To confirm and characterize DIS activity, shapes of ice crystals were observed in the presence of aqueous sucrose solution. First, the samples dissolved in 45 wt. % sucrose solution were sandwiched between two coverslips and frozen at −50° C. After that, the samples were slowly heated at a rate of 0.5° C./min until few ice crystals remained. Then, the samples were cooled at a rate of 0.1° C./min to induce the growth of ice crystals. DFOM images were taken after 10 min of cooling.

1.8 Characterization of Thermal Hysteresis (TH)

To confirm TH activities of the samples, the growth rate of a single ice crystal was monitored under various supercooled temperatures. Briefly, the samples were rapidly cooled to −50° C. using a custom-build nanoliter osmometer to form polycrystalline ice crystals. Then, the temperature was slowly increased until a single ice crystal remained. When the single ice crystal maintains its size for more than 4 min, the temperature was set as a melting point. After that, the temperature was decreased to a target temperature and the growth rate of the ice crystal was measured by monitoring its growth for 4 min. The TH was evaluated as a difference between the melting point and the temperature at which the growth of ice crystal is observed (growth rate>0 μm/min).

1.9 All Atom Molecular Dynamics (AA MD) Simulation

The AA MD simulation was performed with GROMACS v5.1.4 using the CHARMM36 force field. (Abraham, M. J.; Murtola, T.; Schulz, R.; Pall, S.; Smith, J. C.; Hess, B.; Lindahl, E. GROMACS: high performance molecular simulations through multi-level parallelism from laptops to supercomputers. *SoftwareX* 2015, 1, 19-25.; Huang, J.; MacKerell Jr, A. D. CHARMM36 all-atom additive protein force field: validation based on comparison to NMR data. *J. Comput. Chem.* 2013, 34 (25), 2135-2145.). The structure of the oligopeptide was made using MarvinSketch and the parameters were derived using CGenFF (Vanommeslaeghe, K.; MacKerell, A. D. Automation of the CHARMM general force field (CGenFF) I: bond perception and atom typing. *J. Chem. Inf. Model.* 2012, 52 (12), 3144-3154.). Considering the actual melting point (Tm) of ice (272.2 K), a TIP4P/ICE water model was used (Berendsen, H. J. C.; Postma, J. P. M.; van Gunsteren, W. F.; DiNola, A.; Haak, J. R. Molecular dynamics with coupling to an external bath. *J. Chem. Phys.* 1984, 81 (8), 3684-3690.). The Au NCs were designed to include 665 Au atoms (i.e., a side length of 2 nm). The CHARMM-Metal force fields rationalized interactions between the biomolecules at inorganic interfaces (Abascal, J. L.; Sanz, E.; Garcia Fernandez, R.; Vega, C. A potential model for the study of ices and amorphous water: TIP4P/Ice. *J. Chem. Phys.* 2005, 122 (23), 234511.). Au colloids having various sizes and shapes were prepared using a nanocluster builder in Materials Studio (Accelrys Inc., San Diego, CA, 2011). All MD systems were maintained at 1 bar using Berendsen and Parrinello-Rahman algorithms for the equilibrium and production run, respectively (Heinz, H.; Vaia, R. A.; Farmer, B. L.; Naik, R. R. Accurate simulation of surfaces and interfaces of face-centered cubic metals using 12-6 and 9-6 Lennard-Jones potentials. *J. Phys. Chem. C* 2008, 112 (44), 17281-17290.; Parrinello, M.; Rahman, A. Polymorphic transitions in single crystals: a new molecular dynamics method. *J. Appl. Phys.* 1981, 52 (12), 7182-7190.). Neighbour lists were built using a Verlet cut-off scheme with a cut-off radius of 1.2 nm, and were updated at each step. A LINCS algorithm was used to constrain the bond lengths (Hess, B.; Bekker, H.; Berendsen, H. J.; Fraaije, J. G. LINCS: a linear constraint solver for molecular simulations. *J. Comput. Chem.* 1997, 18 (12), 1463-1472.). All simulations were conducted using a leap-frog integrator with a time step of 2 fs. Electrostatic interactions were calculated using PME with a cutoff of 1.2 nm (Darden, T.; York, D.; Pedersen, L. Particle mesh Ewald: An N log (N) method for Ewald sums in large systems. *J. Chem. Phys.* 1993, 98 (12), 10089-10092.).

Small Au NC of 2 nm, large Au NS of 5 nm and large Au NC of 5 nm were made using 665, 3925 and 7813 Au atoms, respectively. The oligopeptides were attached proportionally to the surface area of Au NPs at about 2.5 peptide/nm$^2$. Thereby, 60, 196 and 375 oligopeptides were attached to the small Au NC, large Au NS and large Au NC, respectively.

A continuous ice growth system was built within cells of 10.8 nm×10.4 nm×8.6 nm for small Au colloids of 2 nm, and 14.7 nm×14.9 nm×13.0 nm for large Au colloids of 5 nm, respectively. Seed ice was inserted therein to growth, and fixed disordered water molecules were used to prevent the ice from growing downward.

The utilities in GROMACS and MDAnalysis 20 were used to evaluate hydrogen bonding lifetime analysis. The lifetime for hydrogen bonding between oligopeptides and water/ice molecules was integrated in the period of 298 to 300 ns calculation time. All the possibilities of hydrogen bonding from functional moieties of oligopeptides such as amine, carbonyl, and hydroxyl groups were taken into account. PyMOL (The PyMOL Molecular Graphics System, Version 2.0 Schrödinger, LLC) was used to visualize the simulation results.

1.10 AA MD Simulation for Binding Energy Calculation of Au Colloids with Peptide To calculate the binding energy between the Au colloids with peptide and ice crystal (i.e., a change in a free energy), the pulling system (umbrella sampling simulation) was numerically simulated. To this end, a system box of 10×10×12 nm$^3$ having a total of 200,000 atoms including Au particles, ice surface and liquid water layer was prepared. To generate a z-directional reaction coordinate, the Au particles were pulled from the ice interface about 4 nm for 500 ps using a pulling code in DMP option with a force constant of 1000 kJ/mol nm$^2$. Then, a spacing of the sampling windows was defined as 1 Å and 40 umbrella sampling windows were extracted. Each window is equilibrated for 1 ns, and then carried out 10 NSs of production runs. A potential of mean force (PMF) is obtained using WHAM tools in a GROMACS package. Then, the binding free energy was calculated from a PMF curve as a difference between the highest and lowest energy states.

Example 2. Results and Discussion 2.1 Synthesis of Anti-Freezing Au Colloid

Figure 2A:
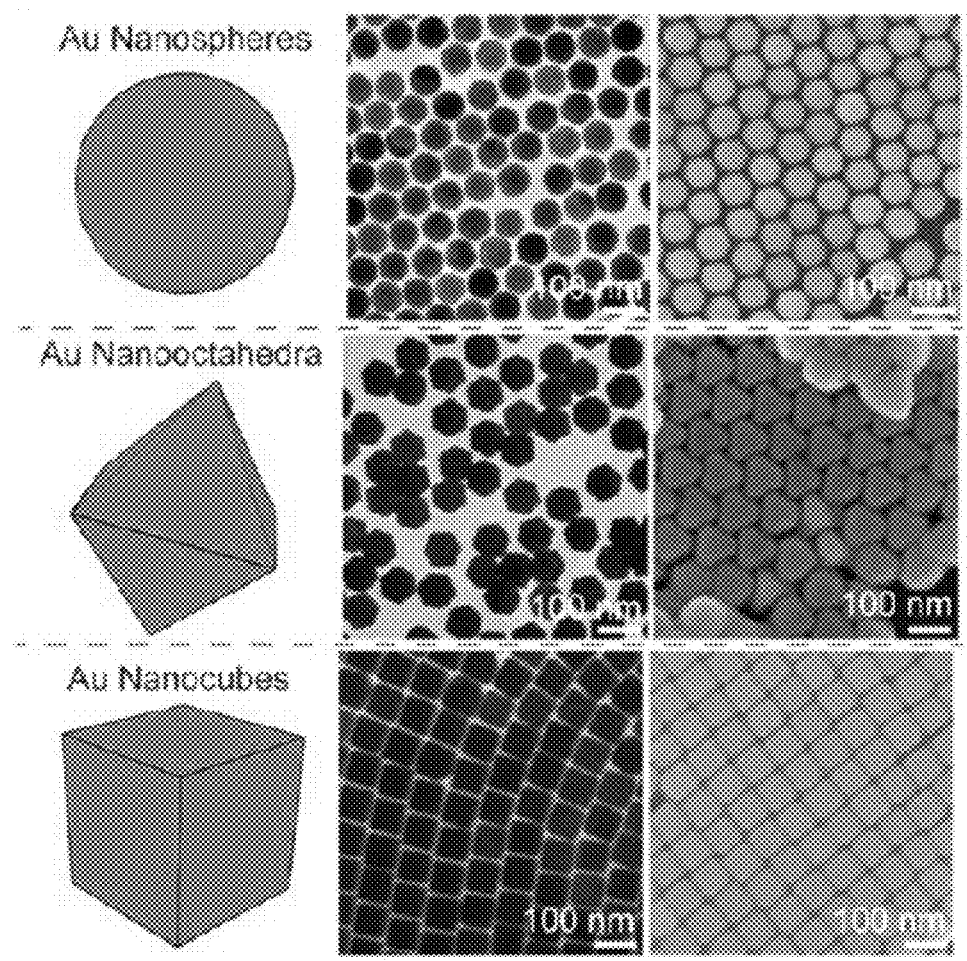
FIG. 2A is transmission electron microscopy and scanning electron microscopy images according to shapes of the Au NPs.
Figure 2B:
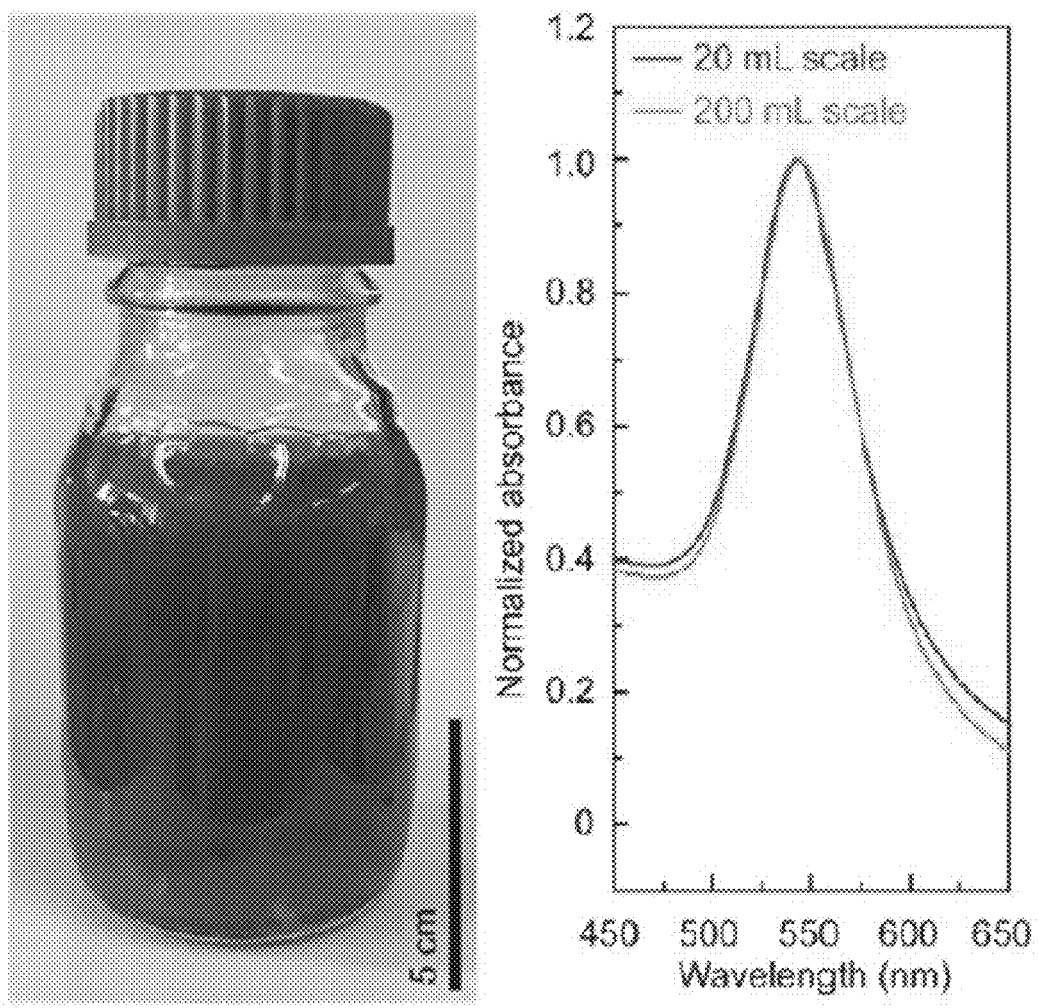
FIG. 2B is a photograph of a large-scale (200 mL) synthetic bath of Au nanospheres and a graph showing corresponding UV-Vis absorption spectra exhibiting that peaks in the synthesis of small-scale (20 mL) and large-scale (200 mL) do not substantially apear.

Au NPs having highly uniform and different shapes were synthesized in sufficiently high yield and scalability. FIG. 2A shows scanning electron microscopy (SEM) and transmission electron microscopy (TEM) images of the Au NPs used in the present invention. To systematically investigate an effect of interfacial contact on the inhibition of ice growth and recrystallization, Au NPs were synthesized so as to have the same size of 75 nm but different shapes, briefly, nanospheres (NSs), nanooctahedra (NOs), and nanocubes (NCs). Through the growth of polygonal-shaped Au colloids and subsequent selective etching of their vertices, highly uniform Au colloids were obtained in a sufficiently large scale (FIG. 2B). The LSPRs of Au NSs were maintained consistently even after scaling up the synthetic batch from 20 mL to 200 mL (see UV-Vis absorption spectra in the right panel of FIG. 2B), thereby providing evidence of both the scalability and reliability of Au colloidal synthesis in the present invention.

Figure 2C:
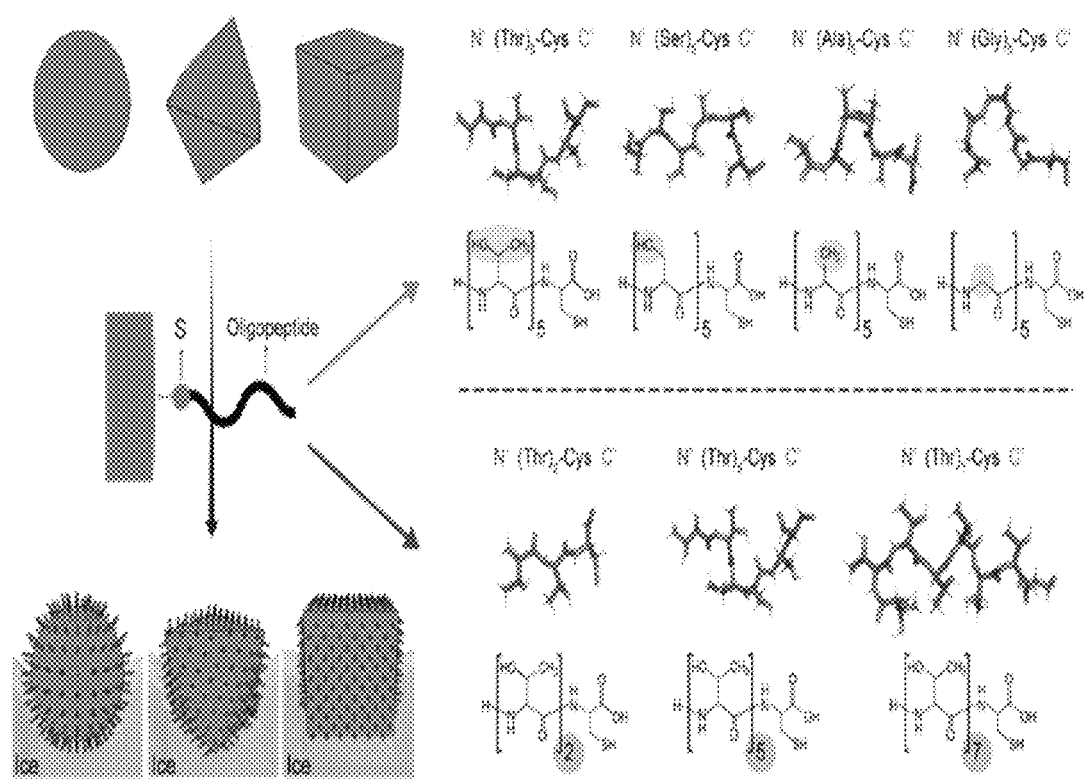
FIG. 2C is views showing thiol-mediated attachment of oligopeptide to surfaces of Au colloids.

Oligopeptides were conjugated to the Au NPs prepared above through a pseudo-covalent bonding between the thiol groups of cysteine and Au. Although the full rationalization route for the interfacial interaction between AF(G)P and ice remains elusive, linearly and regularly arranged functional moieties with both hydrophilicity and hydrophobicity (e.g., Thr) are known to be associated with the inhibition of ice growth and recrystallization (Doxey, A. C.; Yaish, M. W.; Griffith, M.; McConkey, B. J. Ordered surface carbons distinguish antifreeze proteins and their ice-binding regions. *Nat. Biotechnol.* 2006, 24, 852-855.; Garnham, C. P.; Campbell, R. L.; Davies, P. L. Anchored clathrate waters bind antifreeze proteins to ice. *Proc. Natl. Acad. Sci. U.S.A.* 2011, 108, 7363-7367.; Davies, P. L. Ice-binding proteins: a remarkable diversity of structures for stopping and starting ice growth. *Trends Biochem. Sci.* 2014, 39, 548-555.; Meister, K.; Lotze, S.; Olijve, L. L.; DeVries, A. L.; Duman, J. G.; Voets, I. K.; Bakker, H. J. Investigation of the ice-binding site of an insect antifreeze protein using sum-frequency generation spectroscopy. *J. Phys. Chem. Lett.* 2015, 6, 1162-1167.; Dolev, M. B.; Braslaysky, I.; Davies, P. L. Ice-binding proteins and their function. *Annu. Rev. Biochem.* 2016, 85, 515-542.; Hudait, A.; Odendahl, N.; Qiu, Y.; Paesani, F.; Molinero, V. Ice-nucleating and antifreeze proteins recognize ice through a diversity of anchored clathrate and icelike motifs. *J. Am. Chem. Soc.* 2018, 140, 4905-4912.). Oligopeptides, which provide multiple hydrogen-bonding and hydrophobic sites, were directly attached onto the Au NPs (FIG. 2C). Cys-terminated (C') oligopeptides with different sequences were used to systematically investigate the effect of the different moieties on ice growth inhibition, including (Thr)$_n$-Cys, (Ser)$_n$-Cys, (Ala)$_n$-Cys, and (Gly)$_n$ in the order from an N terminus to C terminus. Herein, n was fixed to 5 for a comparison between the respective different oligopeptide sequences in terms of ice growth inhibition. In addition, n was controlled from 2, 5 and 7 for (Thr)$_n$-Cys to investigate effects of n on ice binding and resultant ice growth inhibition. The conformations of the respective oligopeptides shown in FIG. 2C were determined from AA MD simulations. Before conjugating these synthetic oligopeptides, the organic ligands, intrinsically formed on the surface of Au NPs during their synthesis process, were almost removed to avoid their side effects on the interaction with ice.

After mixing the reagents, the conjugation of oligopeptides was spontaneously performed via pseudo-covalent bonding. The attachment of such synthetic oligopeptides onto the Au NPs was in situ monitored during the conjugation process by red-shifted peaks for LSPR extinction, measured by UV-Vis absorption spectroscopy. These LSPR peak shifts equally appeared in all the several simulation results with being consistent (finite-difference time-domain (FDTD) method, shown in FIG. 3).

Note that these attachments of oligopeptides were performed until the LSPR extinction peak was no longer shifted. This implies that oligopeptides were maximally attached onto the Au NPs, briefly, full conjugation, and the present inventors has used the upper bound for ice growth inhibition with these Au NPs.

Figure 3D:
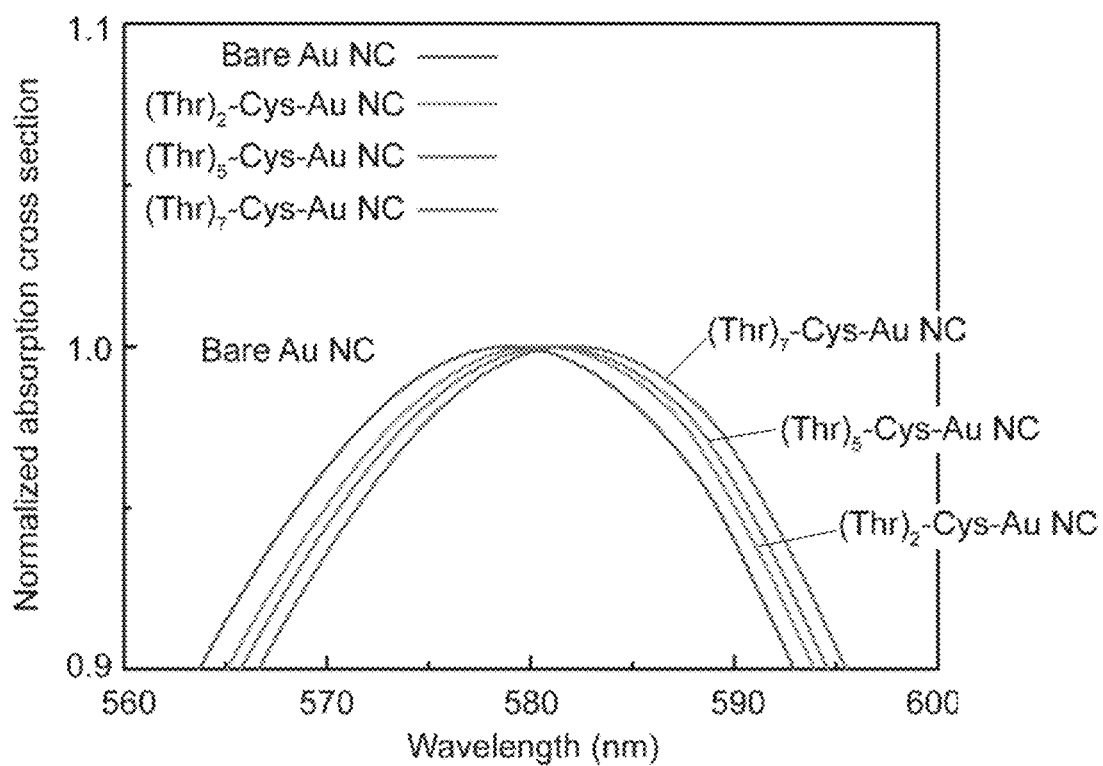

Once n was fixed to 5, an almost consistent red-shifting of the LSPR extinction peaks after the full conjugation was observed regardless of the shapes of Au NPs or oligopeptide sequences. In contrast, the LSPR extinction peak of the longer oligopeptide-conjugated Au NCs was more red-shifted than that of the shorter oligopeptide-conjugated Au NCs (FIG. 3D).

Figure 5A:
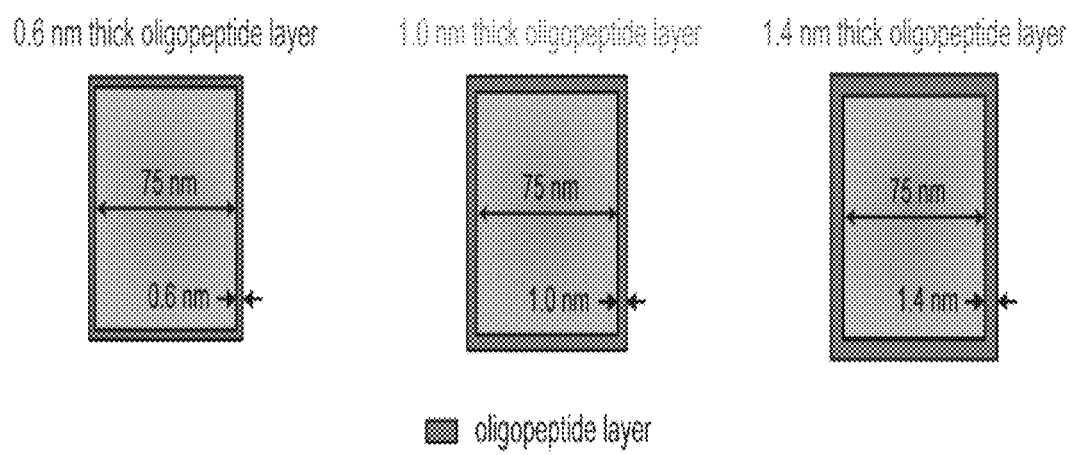
FIG. 5A is views showing simulation models.
Figure 5B:
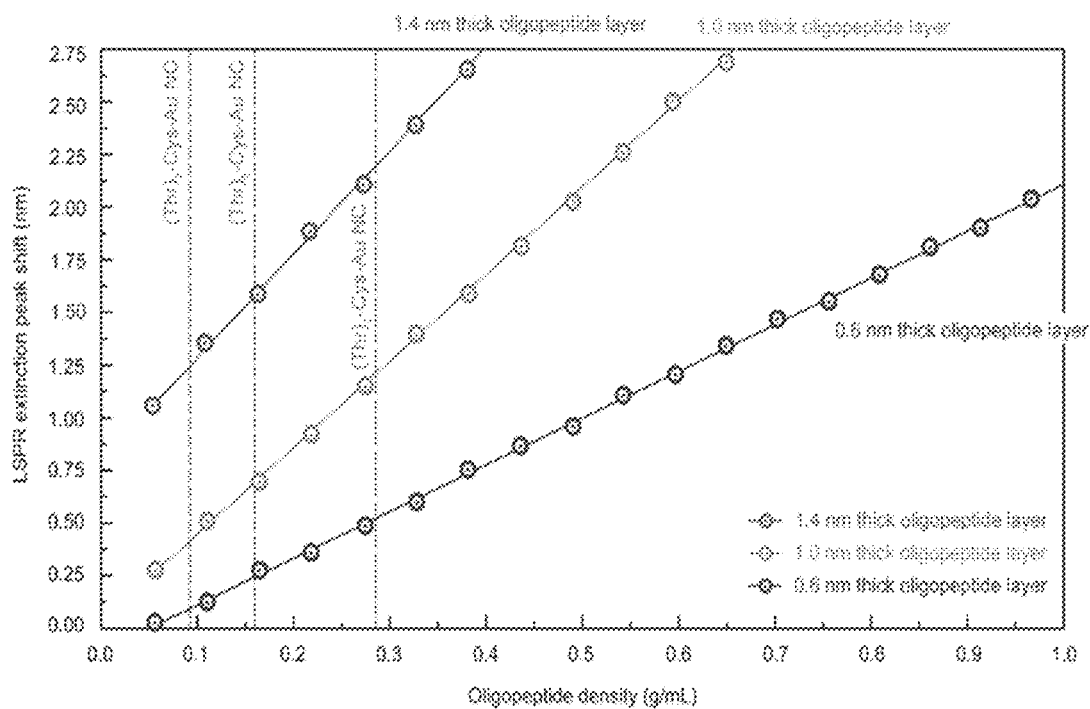
FIG. 5B is a graph showing the calculated results of LSPR extinction peak shifts of oligopeptide-conjugated Au nanocubes (NCs) according to oligopeptide densities.

Then, the attached oligopeptide density was quantified by chemically detaching the oligopeptides from the Au NPs and directly counting the same (FIG. 4). Given n is 5 mer, the number of the attached oligopeptides (i.e., (Thr)$_5$-Cys) was almost consistent in 0.13 to 0.17 per nm$^2$ of Au NP surface regardless of the shapes of Au NPs and the peptide sequences. These results coincide with that the red-shifting of the LSPR extinction peaks appears in almost consistent degree after the conjugation of oligopeptides. An increase in n for Thr causes a reduction in the number of accessible oligopeptides to be attached onto the Au NPs. When the length of oligopeptide is increased from 2 mer to 7 mer, the number of oligopeptides per nm$^2$ of Au NP surface was reduced from about 0.23 to about 0.075, respectively. For longer oligopeptides, electrostatic repulsion and steric hindrance become more significant, and as a result, the maximum density of oligopeptides attachable onto the Au NPs was reduced. The more red-shifted LSPR extinction peaks of the longer oligopeptide-conjugated Au NCs (FIG. 3), even with their relatively lower surface densities, were consistent with the theoretical prediction (FIG. 5); this can be attributed to the fact that the LSPR shift for the longer oligopeptide-conjugated Au NCs is more sensitive to an increase in the oligopeptide density than that of the shorter oligopeptide-conjugated Au NCs.

2.2 Ice Recrystallization Inhibition of Antifreezing Au Colloids.

Next, effects of the oligopeptide-conjugated Au NPs on the ice recrystallization inhibition (IRI) were verified (FIG. 6). To this end, a splat assay (i.e., non-equilibrium, rapid freezing), which is the standard for quantitation of IRI, was performed. (Voets, I. K. From ice-binding proteins to bio-inspired antifreeze materials. *Soft Matter* 2017, 13, 4808-4823.; Biggs, C. I.; Bailey, T. L.; Graham, B.; Stubbs, C.; Fayter, A.; Gibson, M. I. Polymer mimics of biomacromolecular antifreezes. *Nat. Commun.* 2017, 8, 1546.; Wu, S.; Zhu, C.; He, Z.; Xue, H.; Fan, Q.; Song, Y.; Francisco, J. S.; Zeng, X. C.; Wang, J. Ion-specific ice recrystallization provides a facile approach for the fabrication of porous materials. *Nat. Commun.* 2017, 8, 15154.). Specifically, ice slices were prepared by placing drops of DI water onto a cooling stage (−70° C.). Then, an optical microscope (OM) was used in a dark field (DF) mode to verify a spatial distribution of the recrystallized ice grains by size. Based on the DFOM images, the mean largest grain size (MLGS) of the recrystallized ice domain was traced to deduce the IRI behaviors. To avoid false positives possibly caused by the splat assay, a sucrose sandwich assay was also carried out, so as to doubly confirm the IRI behaviors, as observed from the splat assay.

Figure 6A:
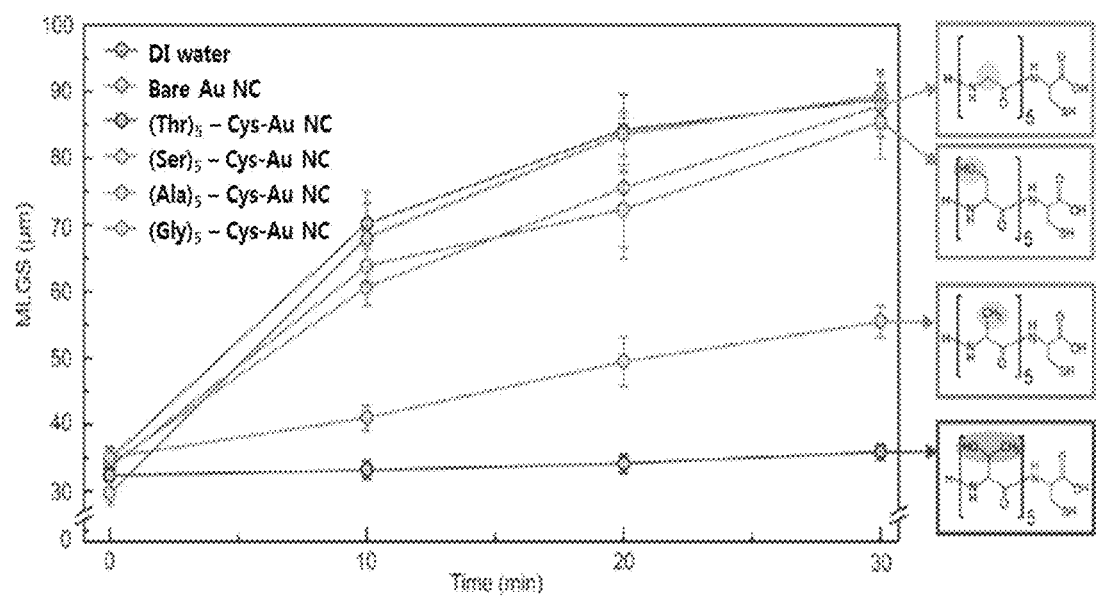
FIG. 6A is a graph showing a mean largest grain size (MLGS) over time of recrystallization of ice crystals from solutions of deionized (DI) water and Au NCs.
Figure 6B:
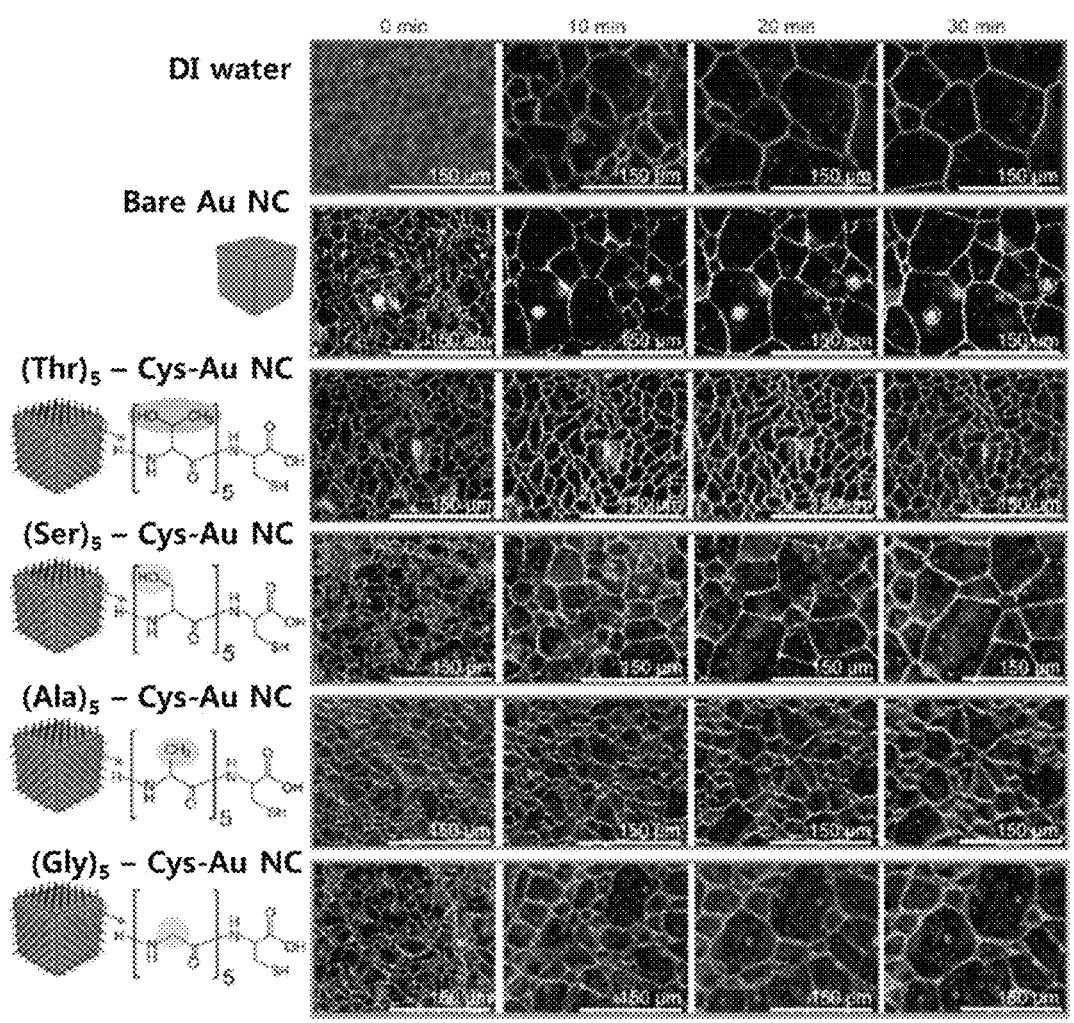
FIG. 6B is views showing dark-field optical microscopy (DFOM) images of recrystallized ice from DI water ($1^{st}$ row), bare Au NC suspension ($2^{nd}$ row), $(Thr)_5$-Cys- ($3^{rd}$ row), $(Ser)_5$-Cys- ($4^{th}$ row), $(Ala)_5$-Cys- ($5^{th}$ row), and $(Gly)_5$-Cys-($6^{th}$ row) conjugated Au NCs suspensions.
Figure 7:
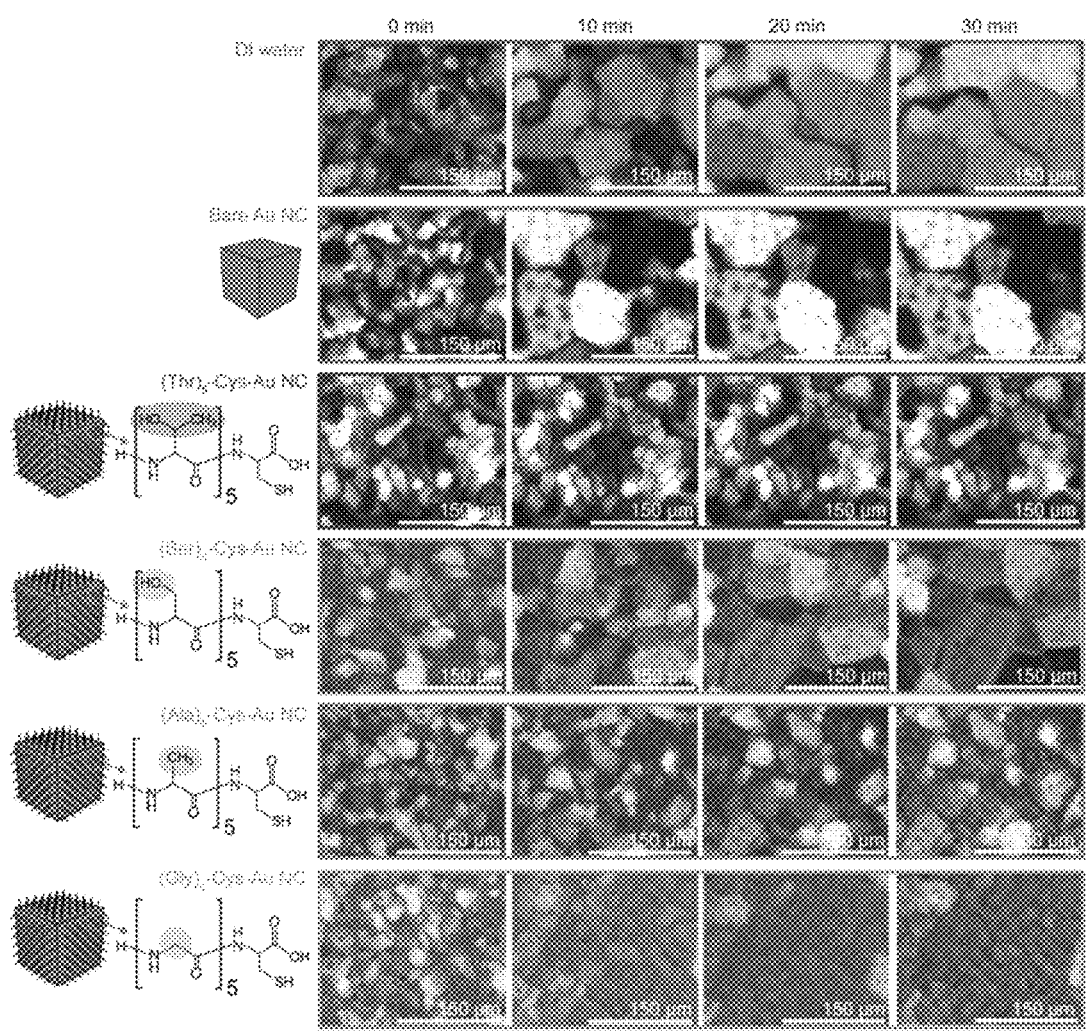
FIG. 7 is views showing bright field polarized optical microscope (BFPOM) images obtained from DI water ($1^{st}$ row), bare Au NC suspension ($2^{nd}$ row), $(Thr)_5$-Cys- ($3^{rd}$ row), $(Ser)_5$-Cys- ($4^{th}$ row), $(Ala)_5$-Cys- ($5^{th}$ row), and $(Gly)_5$-Cys- ($6^{th}$ row) conjugated Au NCs suspensions.

Similar to Ostwald ripening (Gibson, M. I. Slowing the growth of ice with synthetic macromolecules: beyond antifreeze (glyco) proteins. *Polym. Chem.* 2010, 1, 1141-1152.; Budke, C.; Heggemann, C.; Koch, M.; Sewald, N.; Koop, T. Ice recrystallization kinetics in the presence of synthetic antifreeze glycoprotein analogues using the framework of LSW theory. *J. Phys. Chem.* B 2009, 113, 2865-2873.; Budke, C.; Dreyer, A.; Jaeger, J.; Gimpel, K.; Berkemeier, T.; Bonin, A. S.; Nagel, L.; Plattner, C.; DeVries, A. L.; Sewald, N.; Koop, T. Quantitative efficacy classification of ice recrystallization inhibition agents. *Cryst. Growth Des.* 2014, 14, 4285-4294.), recrystallization led to a continuous increase in the ice grain size for an annealing time of 30 min (time-traced MLGS in FIG. 6a, and corresponding DFOM images in 1st row of FIG. 6b). After annealing for 30 min, about 89 µm of MLGS was observed. Adding bare Au NCs in a concentration of 0.2 nM negligibly influenced the ice recrystallization (FIG. 6a, $2^{nd}$ row of FIG. 6b). Note that each ice domain has a single crystallinity, as confirmed by the BFPOM analysis shown in FIG. 7. Reddish cracks within each ice domain originated from the aggregated and trapped bare Au NCs between the substrate and the growing single crystalline ice. This result indicates that the bare Au NCs without oligopeptide have a negligible affinity with the recrystallizing ice crystals.

On the one hand, when adding oligopeptide-conjugated Au NCs, ice grain recrystallization was significantly inhibited in the same concentration (0.2 nM). The IRI behaviors of the Au NCs with different oligopeptides such as $(Thr)_5$-Cys, $(Ser)_5$-Cys, $(Ala)_5$-Cys, and $(Gly)_5$-Cys are highlighted respectively by green, red, orange, and purple colors in FIG. 6a, and corresponding DFOM images are shown in FIG. 6b. Notably, $(Thr)_5$-Cys-conjugated Au NCs were found to dramatically reduce the MLGS and exhibit a higher effect than other 5 mer oligopeptides in terms of IRI. $(Ser)_5$-Cys- and $(Gly)_5$-Cys-conjugated Au NCs negligibly induced IRI activity (MLGS: 85 to 87 µm), while IRI activity was moderately induced by $(Ala)_5$-Cys-conjugated Au NCs (MLGS: about 55 µm).

Figure 8A:
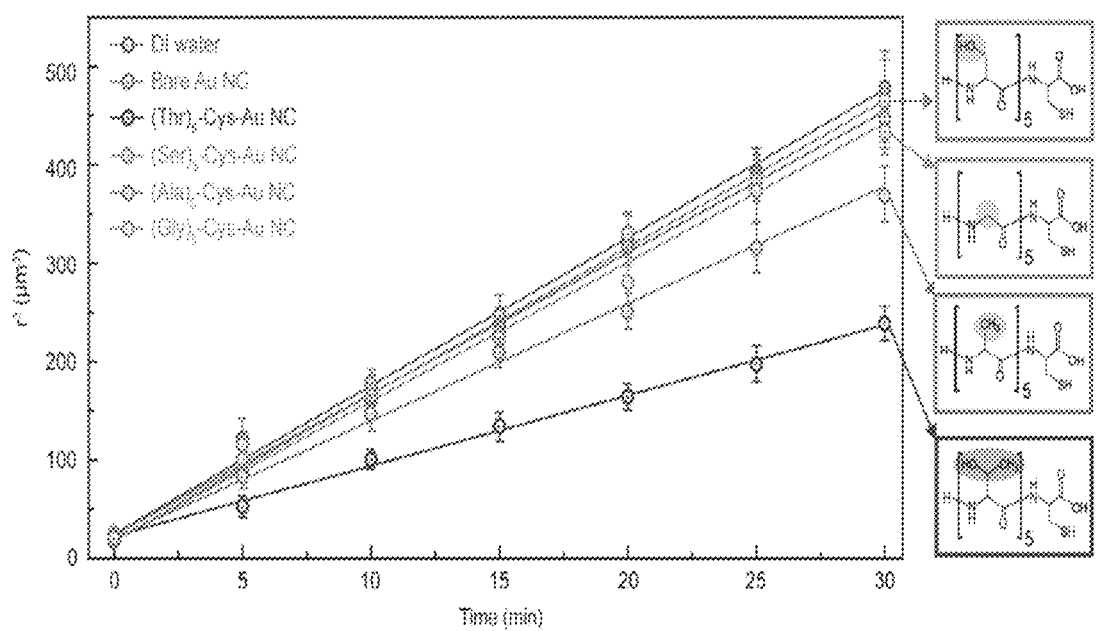
FIG. 8A is a graph showing time-dependent cubed average radius of ice grains of DI water, bare Au NC suspension, $(Thr)_5$-Cys-, $(Ser)_5$-Cys-, $(Ala)_5$-Cys-, and $(Gly)_5$-Cys-conjugated Au NCs suspensions.
Figure 8B:
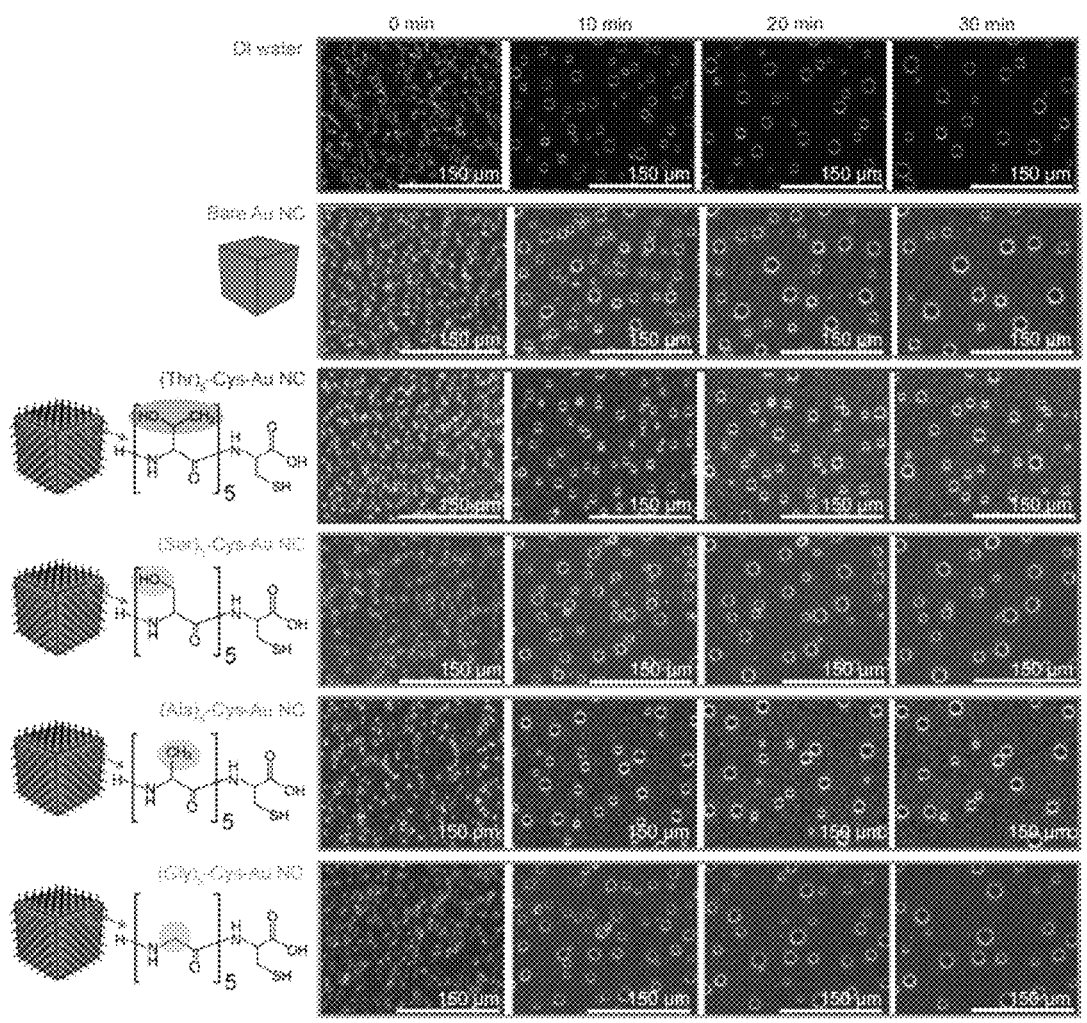
FIG. 8B is views showing DFOM images corresponding to the respective NCs.

Compared with Ser and Gly, Thr is more hydrophobic due to additional methyl groups provided at its graft, while simultaneously, Thr is more hydrophilic than Ala due to hydroxyl groups provided at its graft. Overall, it can be concluded that Thr is more well balanced between hydrophilicity and hydrophobicity than Ser, Ala, and Gly. In this aspect, both hydroxyl and methyl groups of $(Thr)_5$ can cooperatively contribute to the ice binding. The results of the sucrose sandwich assay provided further evidence of a distinct IRI effect for $(Thr)_5$-Cys-conjugated Au NCs, which is significantly contrasted with $(Ser)_5$-Cys-, $(Ala)_5$-Cys-, and $(Gly)_5$-Cys-conjugated Au NCs (FIG. 8).

Figure 9A:
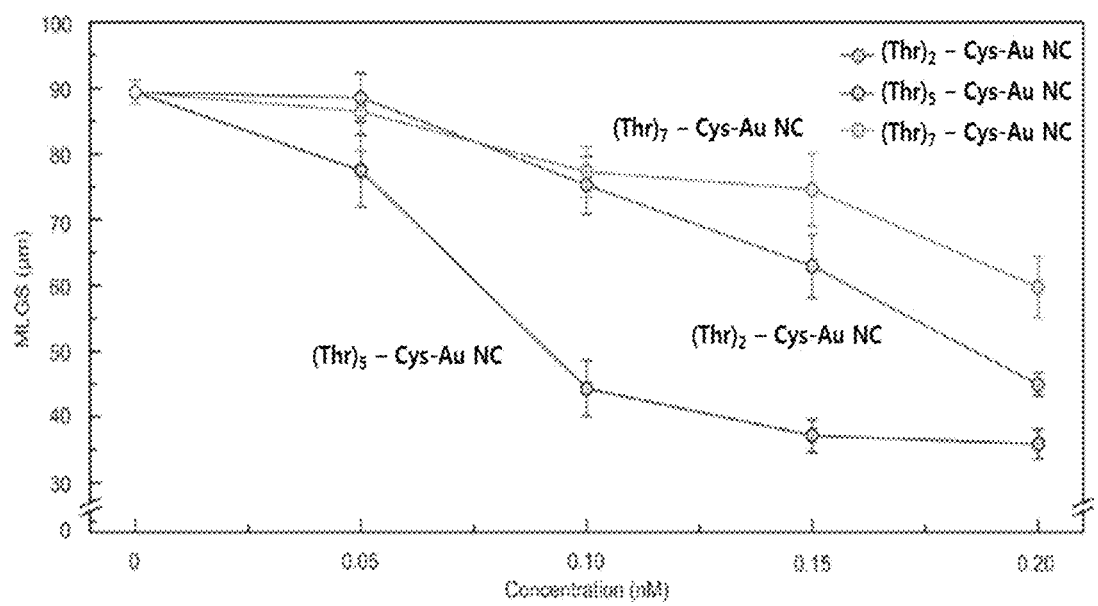
FIG. 9A is a graph showing MLGS values of the recrystallized ice domain for 30 minutes according to the concentration of $(Thr)_n$-Cys-conjugated Au NCs.
Figure 9B:
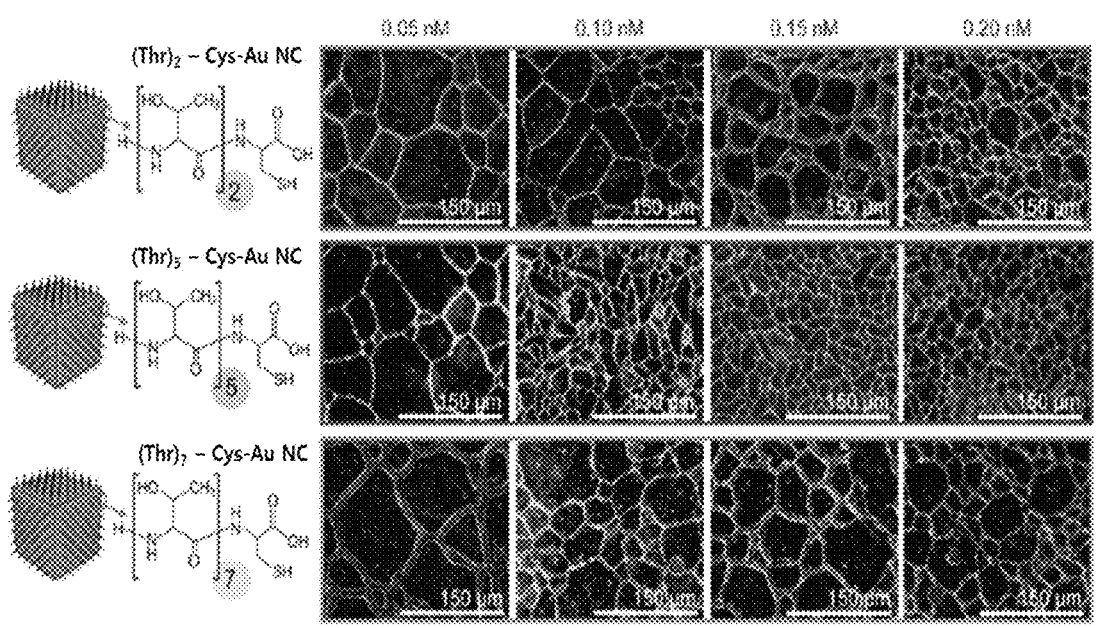
FIG. 9B is views showing $(Thr)_n$-Cys-binding DFOM images of recrystallized ice when n is 2, 5, and 7 in the Au NCs, respectively.
Figure 10A:
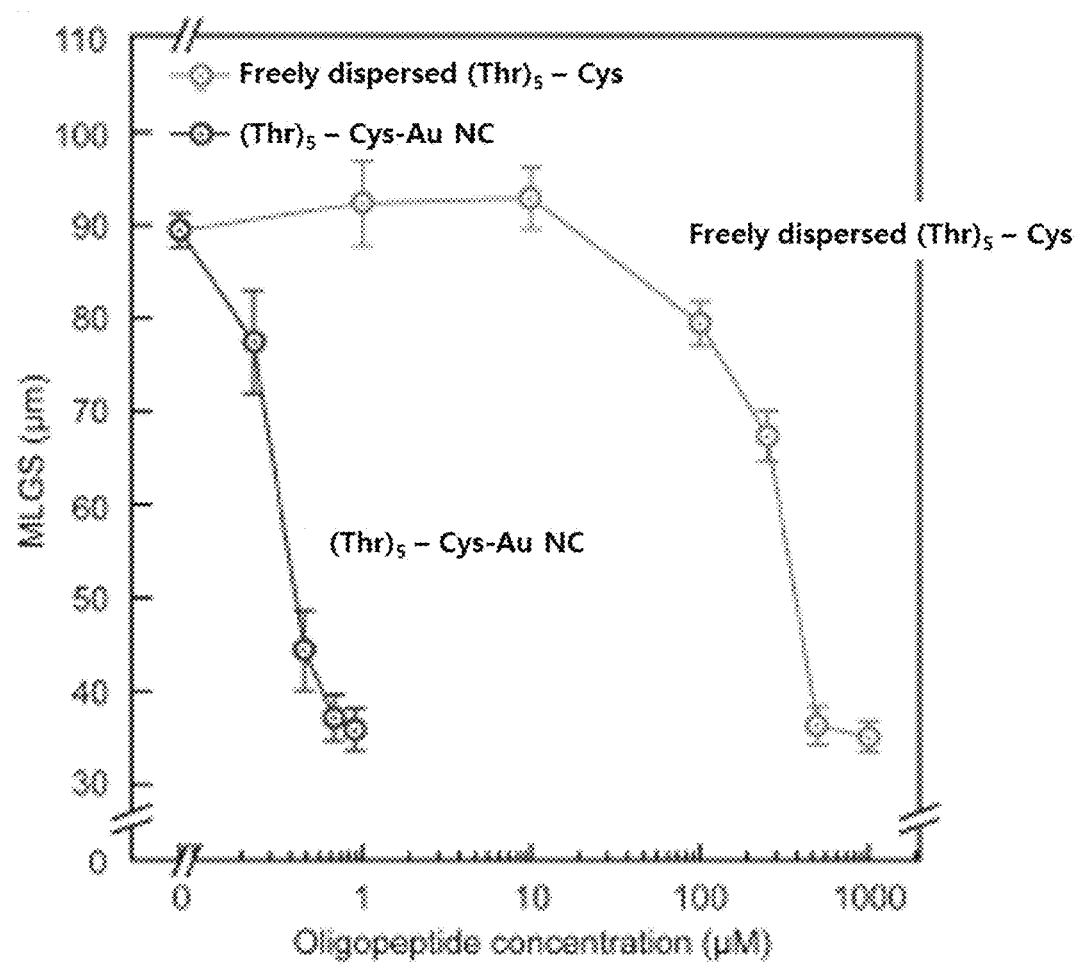
FIG. 10A is a graph showing MLGS of recrystallized ice according to oligopeptide concentration.
Figure 10B:
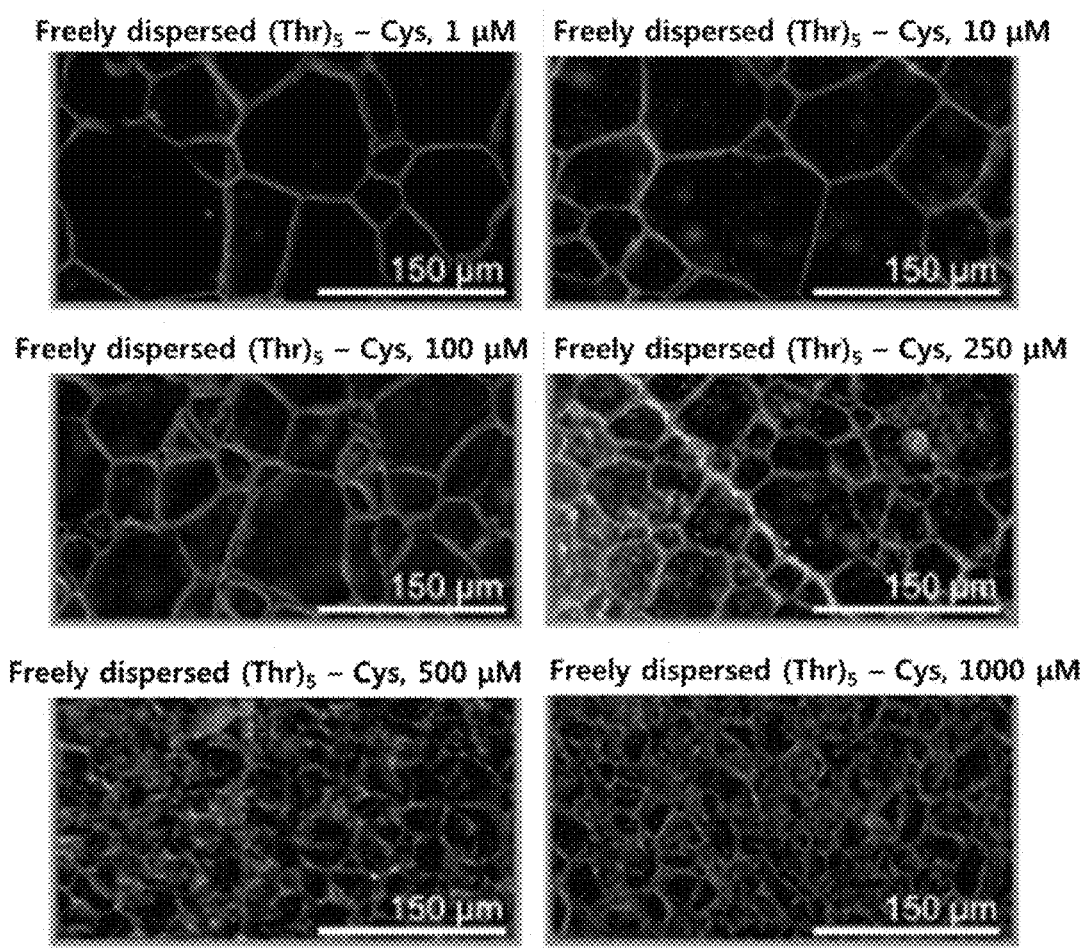
FIG. 10B is views showing DFOM images of recrystallized ice crystals containing 1, 10, 100, 250, 500, and 1000 μM (in the order from an upper left to a lower right)

Further, it has been shown that, unlike the colligative behavior of organic molecular cryoprotectants such as propylene glycol, dimethyl sulfoxide (DMSO), ethylene glycol (EG), and glycerol, for example, the tendency of MLGS to be reduced was gradually saturated according to the concentration of the $(Thr)_5$-Cys-conjugated Au NCs from about 0.15 nM (FIGS. 9a and b). As described above, the density of $(Thr)_5$-Cys, hybridized with Au NCs, was about 0.13 per $nm^2$ of Au NC surface; and when the concentration of the oligopeptide-conjugated Au colloids is 0.2 nM, a total concentration of $(Thr)_5$-Cys, attached onto Au NCs, was about 0.87 µM. When 0.87 µM of $(Thr)_5$-Cys is freely dispersed in DI water without Au NC-mediated organization, any IRI activity could not observed (FIG. 10). IRI was started to appear beyond 100 µM for the freely dispersed $(Thr)_5$-Cys, and the IRI activity is also increased with the concentration of $(Thr)_5$-Cys is increased. A minimum concentration of molecules required to exhibit IRI was $10^2$ fold higher than that of $(Thr)_5$-Cys attached onto the Au NCs, thereby implying that antifreezing moieties attached to a flat geometry of the Au NCs may interact far better on growing ice crystals and subsequently inhibit the ice recrystallization.

In addition, effects of the Thr monomer number (n) of oligopeptide-conjugated Au NCs on IRI were evaluated (FIGS. 9a and b). The 5 mer was found to outperform the 7 mer. This can be attributed to the fact that 5 mer Thr was more readily attached to the Au NCs (about 0.13 per $nm^2$ of Au NC surface) than the 7 mer Thr (about 0.075 per $nm^2$ of Au NC surface). Interestingly, despite the much smaller number of attached oligopeptides, Au NCs with $(Thr)_5$ also outperformed the $(Thr)_2$-Cys-conjugated Au NCs (about 0.23 per $nm^2$ of Au NC surface) in terms of IRI, the reason is that these $(Thr)_5$-Cys-conjugated Au NCs can still have a higher number of Thr moieties than the $(Thr)_2$-Cys-conjugated Au NCs. This result matched well with the results from molecular dynamics (MD) simulation to be described below.

Figure 11A:
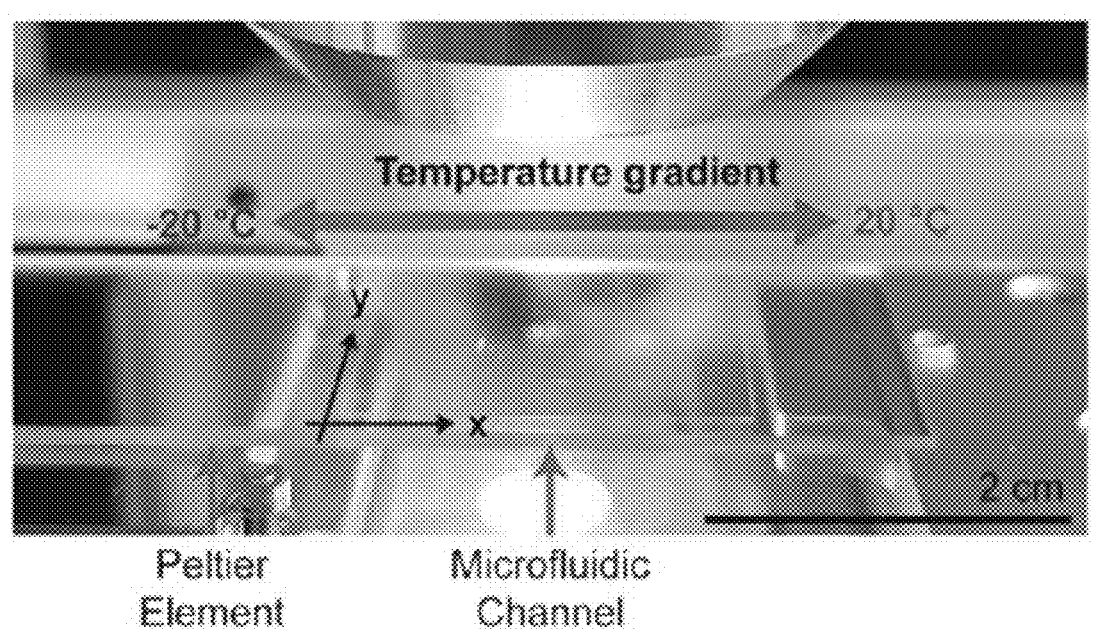
FIG. 11A is a photograph taken to show a cooling apparatus used for directional growth of single crystalline ice.
Figure 11B:
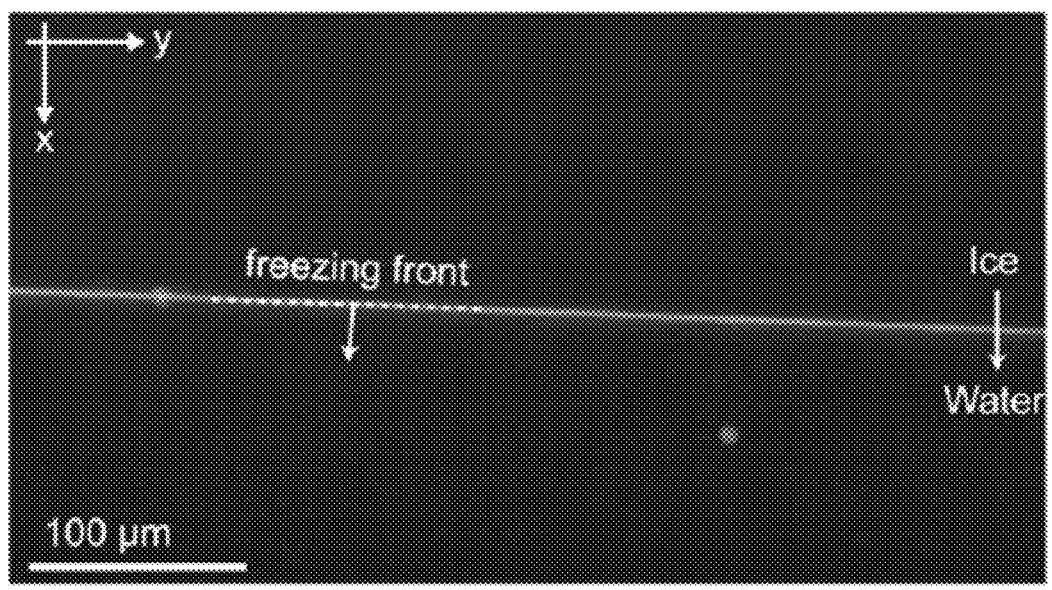
FIG. 11B is a photograph taken using FIG. 11A to show a DFOM image of growing single crystalline ice, FIG. 11C a photograph showing a DFOM image of ice crystals growing in a solution containing bare Au NCs (left), and a photograph showing DF microscope scattering spectra selectively taken in a water-ice interface with randomly accumulated bare Au NCs, and supercooled water with uniformly dispersed Au NCs (right)
Figure 12:
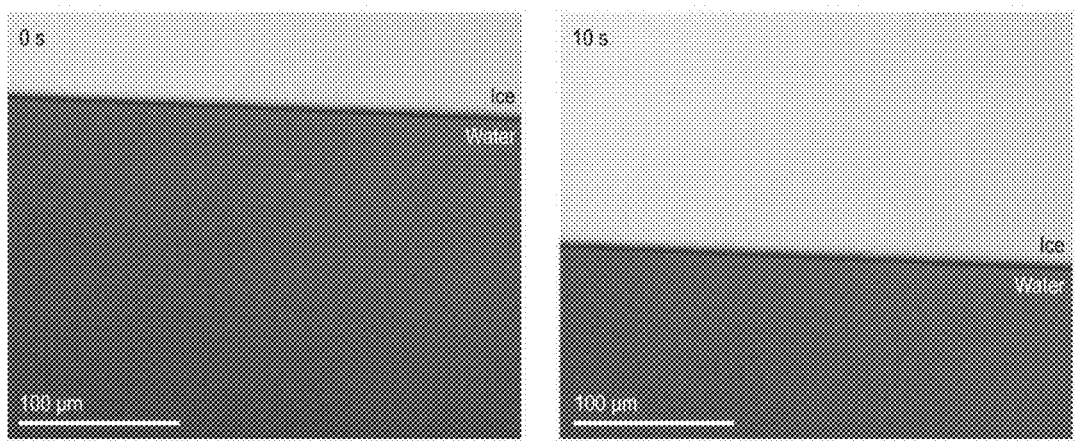
FIG. 12 is photographs showing time-lapse bright field polarized optical microscope (BFPOM) imgaes corresponding to FIG. 11 (b)
Figure 13A:
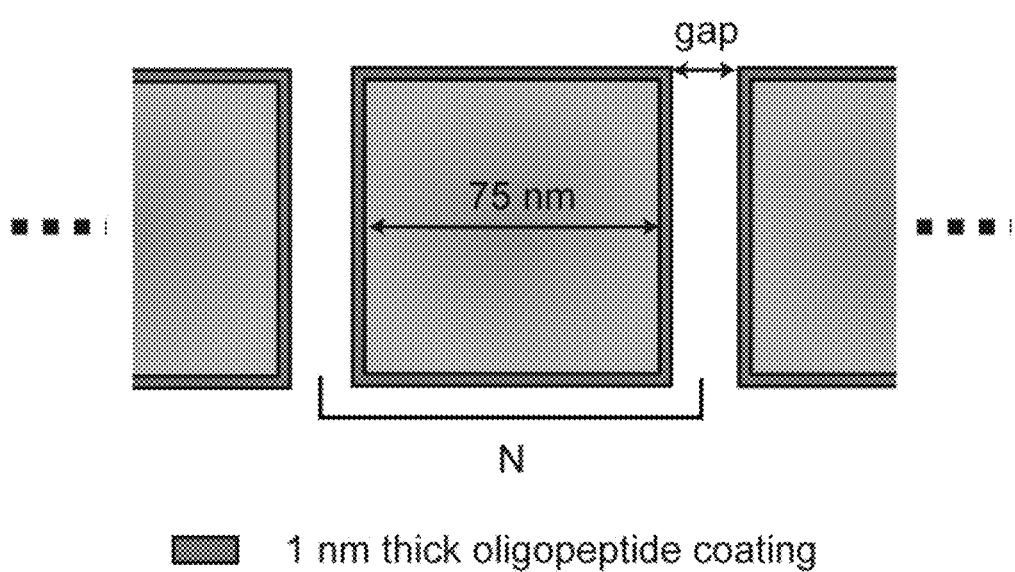
FIG. 13A is a view showing a simulation model, and graphs FIG. 13B to FIG. 13E showing numerically simulated DF scattering spectra of $(Thr)_5$-Cys-conjugated Au NCs and clusters thereof.
Figure 13B:
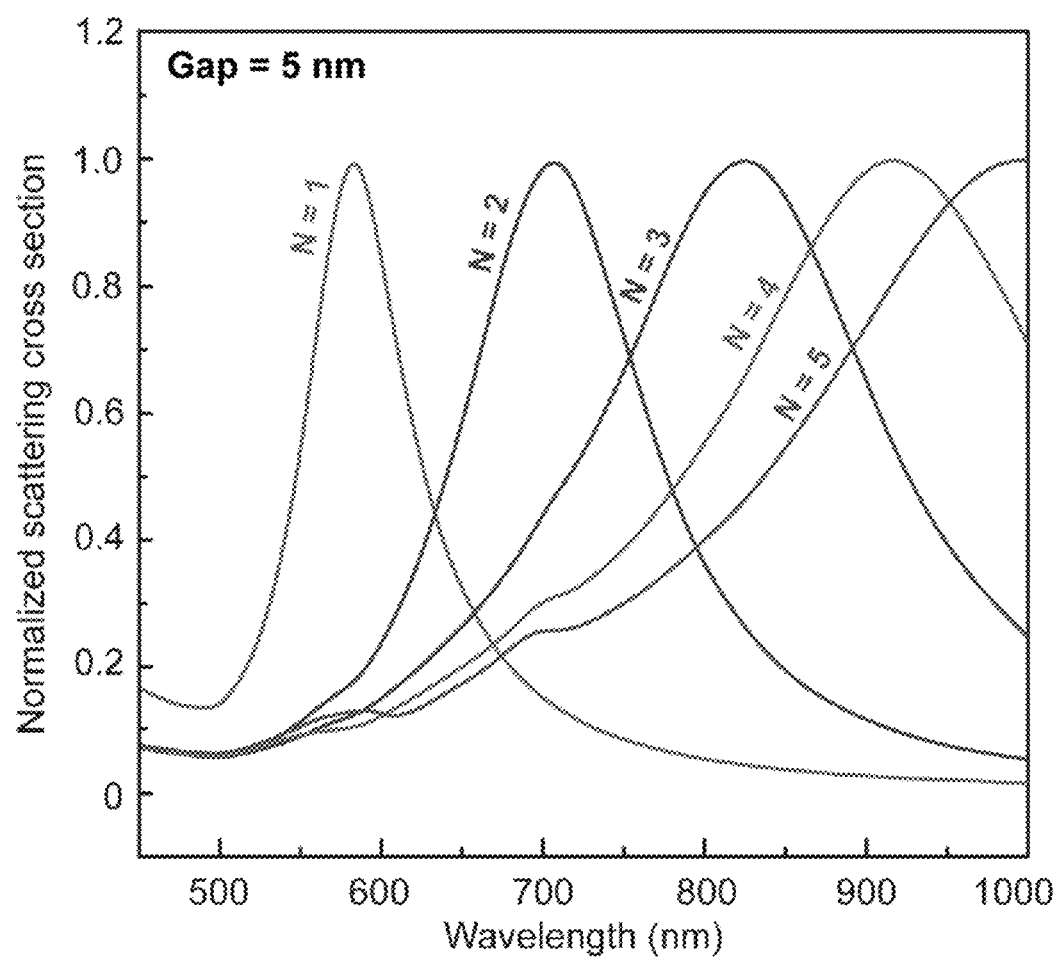
Figure 13C:
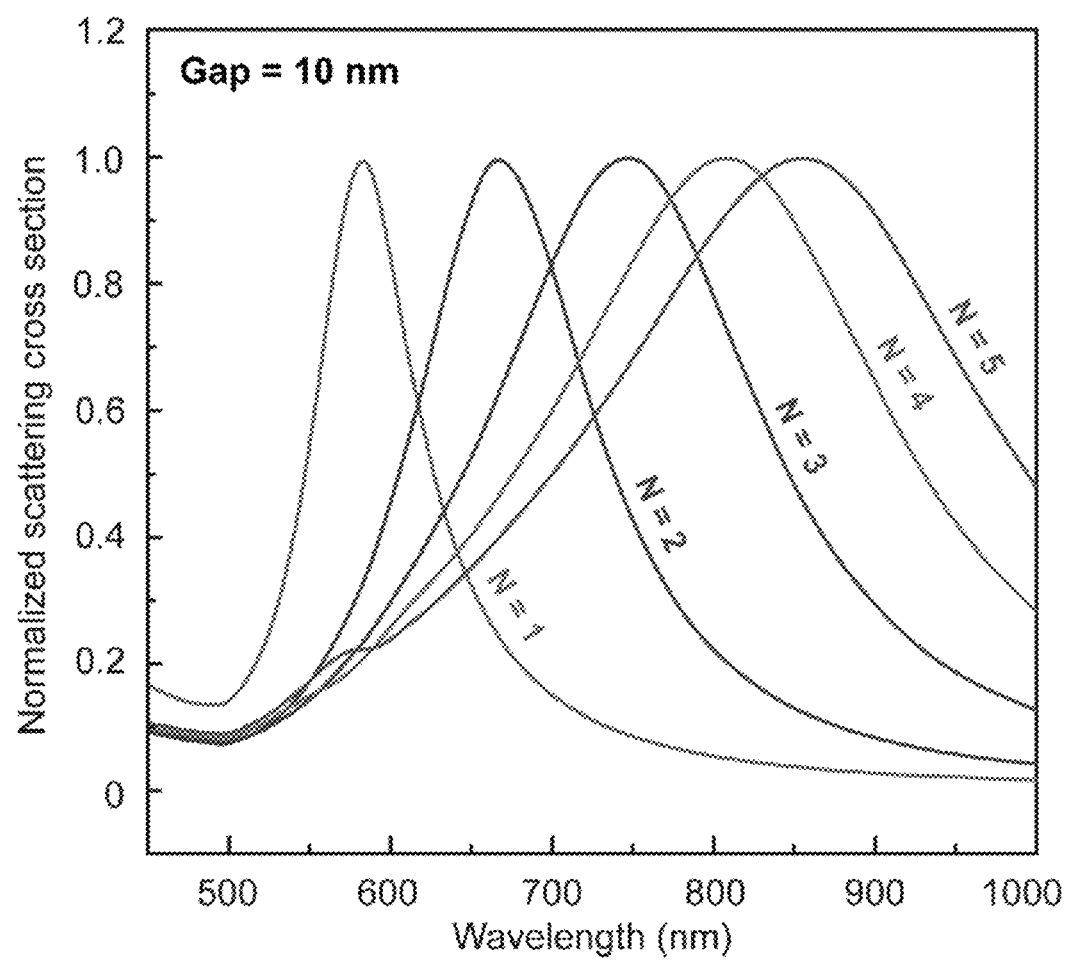
Figure 13D:
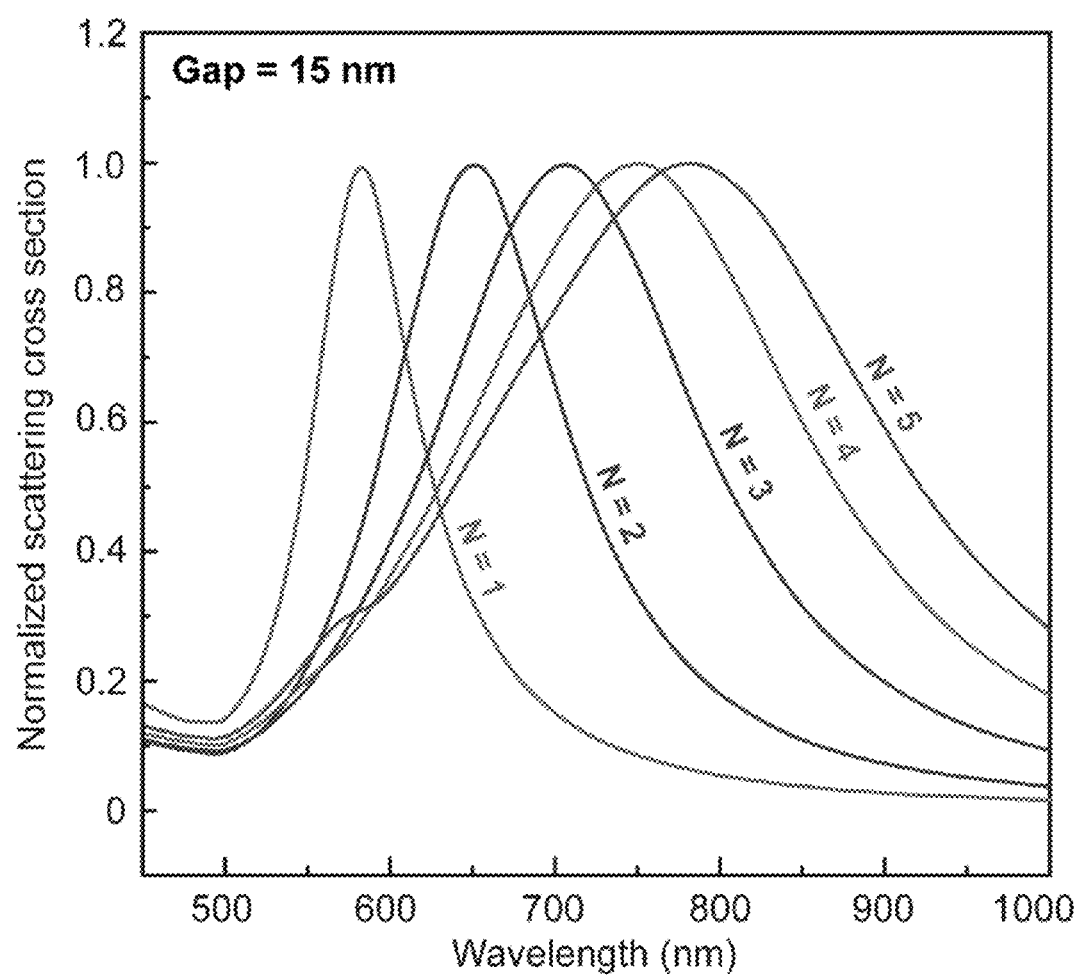
Figure 13E:
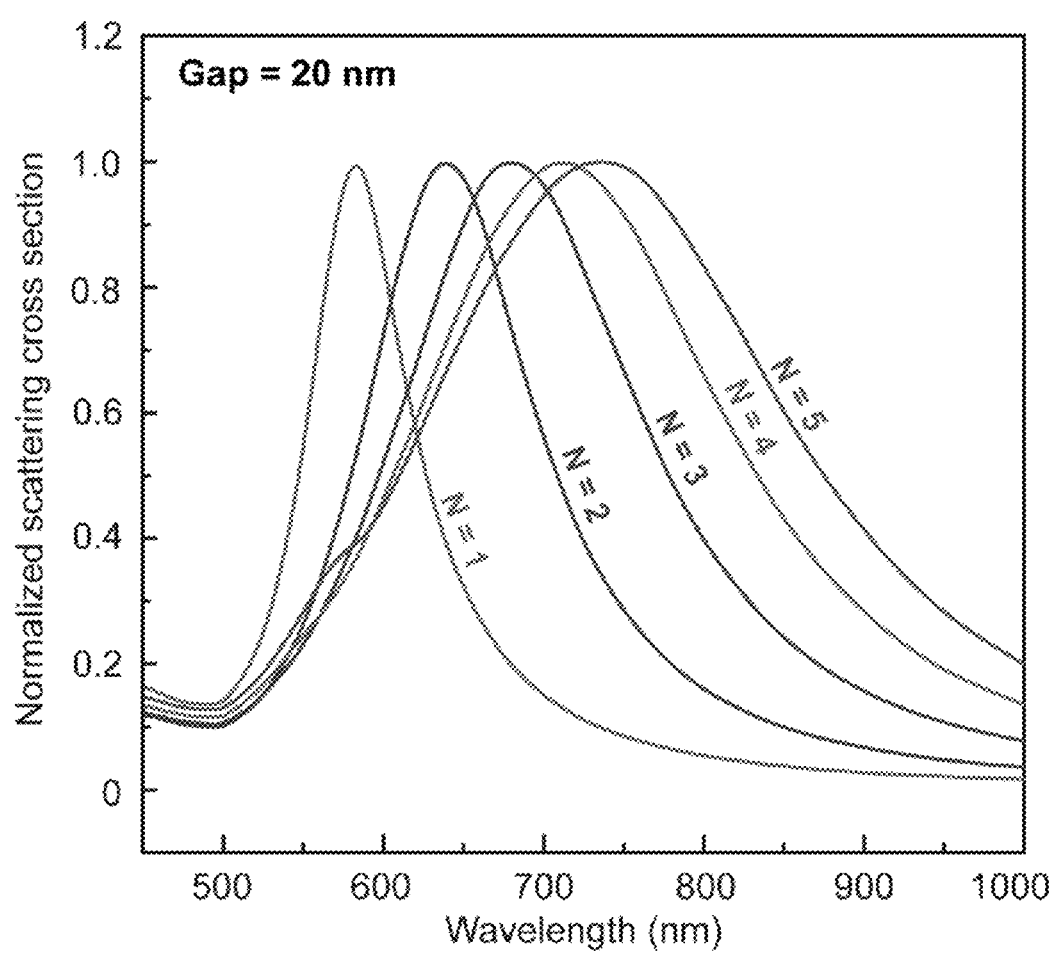
Figure 14:
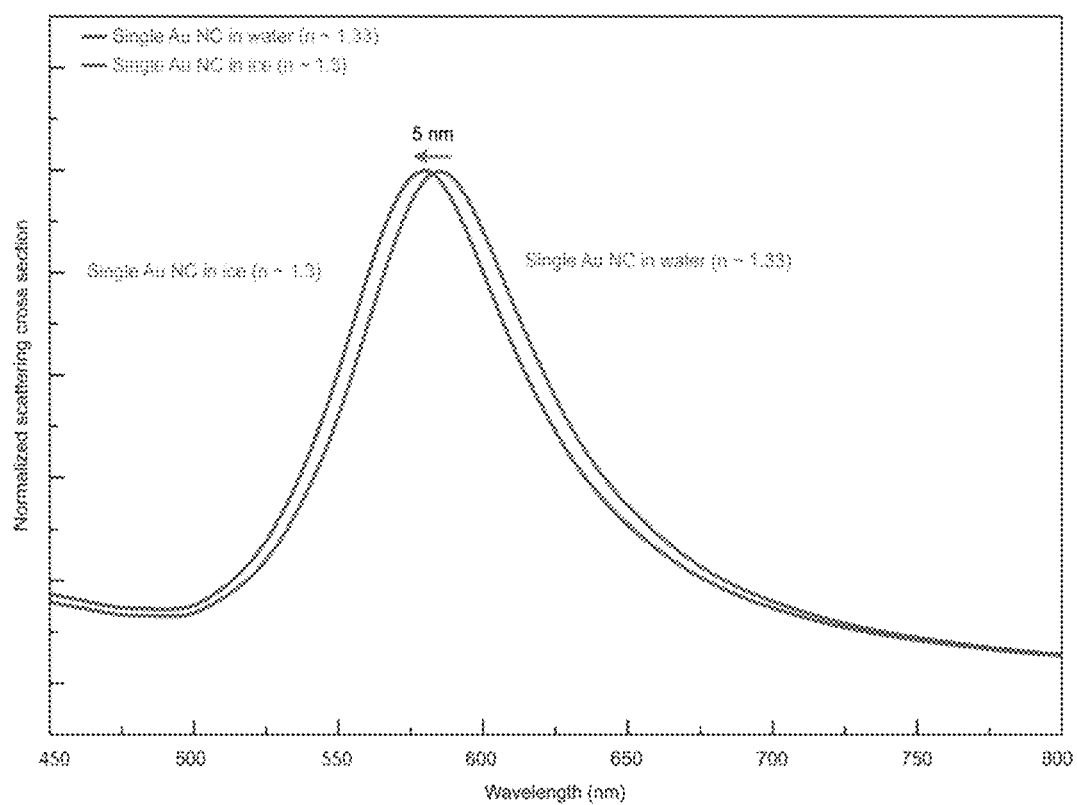
FIG. 14 is a graph showing finite-difference, time-domain (FDTD) calculations of DF scattering of An NCs dispersed in ice and water.

Further, such a significant difference in the ice affinity between bare Au NCs and $(Thr)_5$-Cys-conjugated Au NCs was also confirmed under environments of continuous and slow crystallization (except for recrystallization) of ice at about the melting temperature (Tm), rather than rapid cooling at temperatures much below Tm. To this end, the present inventors have used a cooling stage as shown in FIG. 11a. In particular, the temperature was locally reduced below −20° C. on one side using a Peltier device, while the other side remained at 15 to 20° C. In this way, 4 cm of spatial temperature gradient was induced from −20° C. to room temperature. DI water was introduced into a glass microfluidic channel located in the above device to induce gradual growth of single crystalline ice from −20° C. to ambient temperature area (FIG. 11b). The absence of a grain boundary (FIG. 11b) in conjunction with single colored bright field polarized optical microscope (BFPOM) images (FIG. 12) provided evidence of the single crystallinity of the growing ice.

Figure 11C:
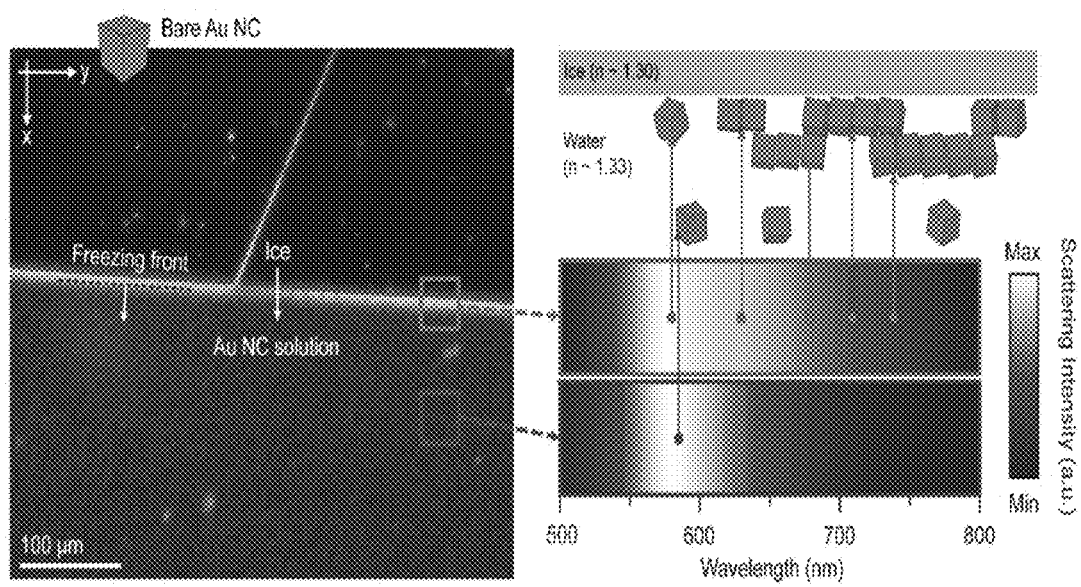
FIG. 11D is a photograph showing a DFOM image of ice crystals growing in a solution containing $(Thr)_5$-Cys-conjugated Au NCs (left), and a photograph showing DF microscope scattering spectra taken in ice and supercooled water region of $(Thr)_5$-Cys-conjugated Au NCs (right)
Figure 11D:
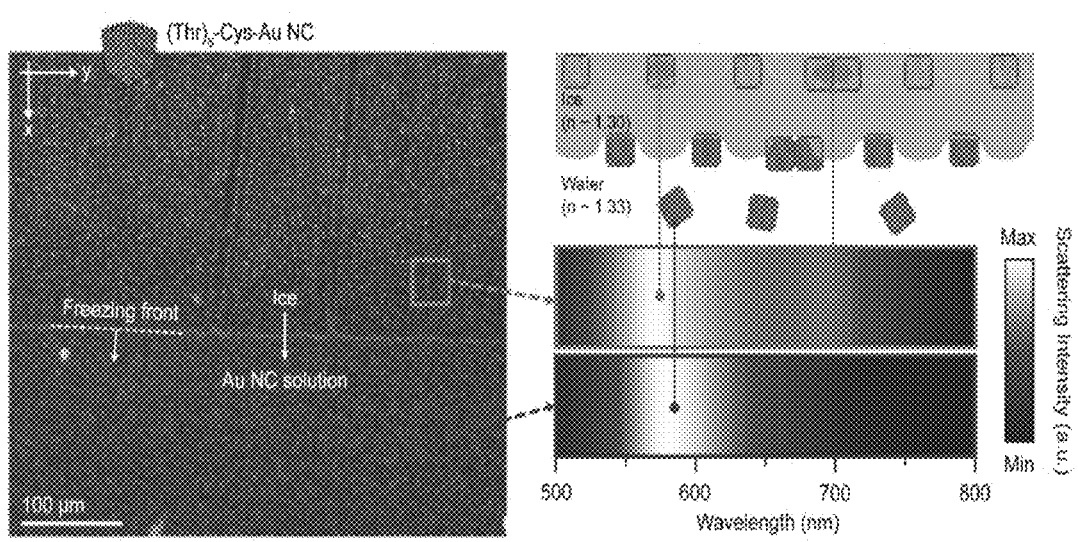
Figure 15A:
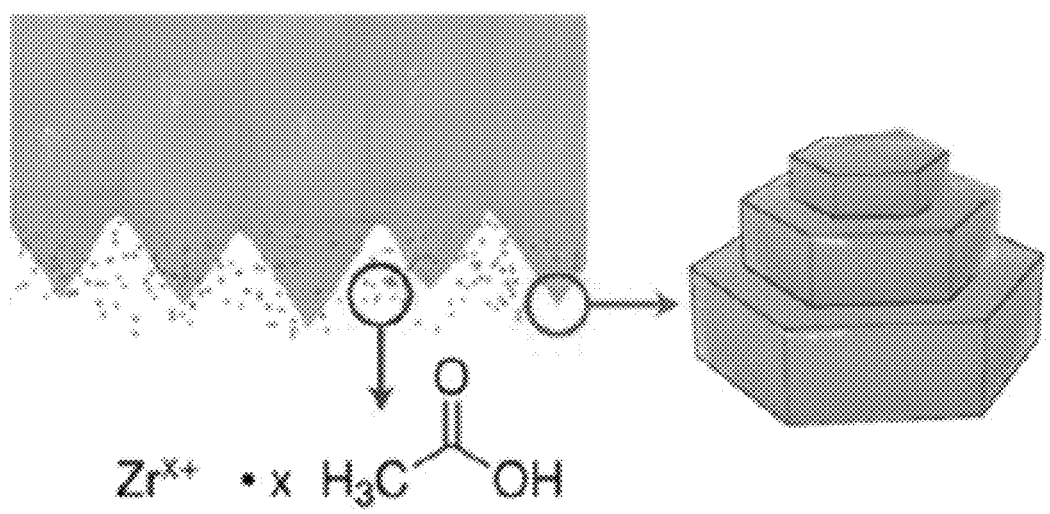
FIG. 15A is a simplified diagram showing DIS activity of ZrAc.
Figure 15B:
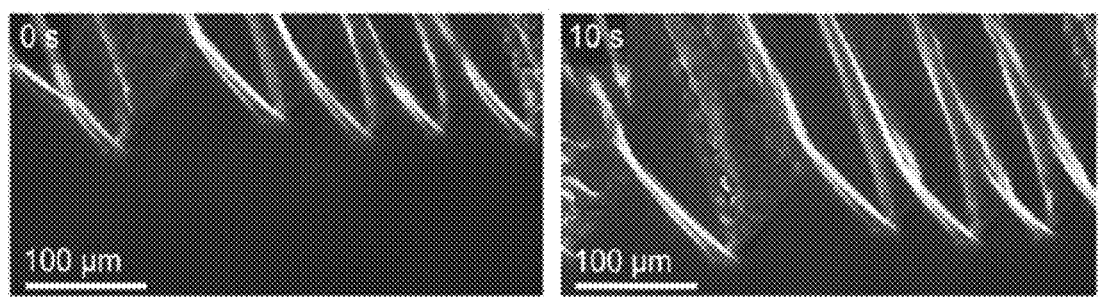
FIG. 15B is photographs showing directionally growing ice containing 20 mg/ml of ZrAc at 0 and 10 seconds.

During this directional growth of single crystalline ice, bare Au NCs were found to be pushed away from the growing ice crystal and randomly accumulated at the interfaces between ice and water (FIGS. 11c and d). On the other hand, $(Thr)_5$-Cys-conjugated Au NCs were spontaneously engulfed within the growing single crystalline ice (FIGS. 11e and f). In particular, it has been confirmed that the $(Thr)_5$-Cys-conjugated Au NCs were homogeneously distributed within the growing ice crystals. In this aspect, it is considered that the AF(G)P-inspired oligopeptides of $(Thr)_5$ play a pivotal role in improvement of interfacial contact between ice and Au NCs and the resultant IRI effect. As seen from the DFOM images, the monomeric and dimeric $(Thr)_5$-Cys-conjugated Au NCs were homogeneously dispersed within the growing ice, whereas various cluster motifs of the bare Au NCs spanning from monomer to pentamer were randomly aggregated at the water/ice interface (FIGS. 11, 13 and 15).

Figure 15C:
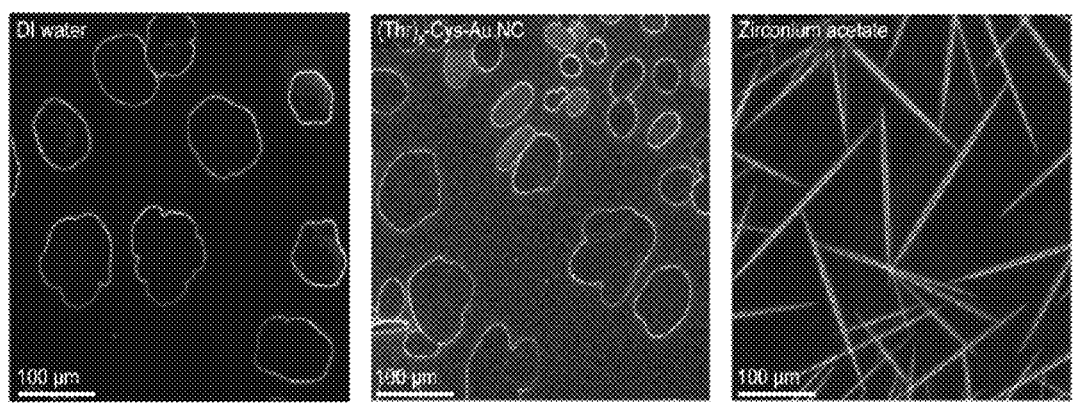
FIG. 15C is photographs showing sucrose assisted DIS analysis results for DI water, 0.20 nM of $(Thr)_5$-Cys-Ac NCs, and 20 mg/ml of ZrAc.

Note that (Thr)$_5$-Cys was randomly organized onto the Au NCs, which is significantly contrasted with the antifreezing moieties of AF(G)P. The regularity of the antifreezing moieties of AF(G)P may be effectively commensurate with an ice crystallinity. (Garnham, C. P.; Campbell, R. L.; Davies, P. L. Anchored clathrate waters bind antifreeze proteins to ice. *Proc. Natl. Acad. Sci. U.S.A.* 2011, 108, 7363-7367.; Meister, K.; Lotze, S.; Olijve, L. L.; DeVries, A. L.; Duman, J. G.; Voets, I. K.; Bakker, H. J. Investigation of the ice-binding site of an insect antifreeze protein using sum-frequency generation spectroscopy. *J. Phys. Chem. Lett.* 2015, 6, 1162-1167.; Hudait, A.; Odendahl, N.; Qiu, Y.; Paesani, F.; Molinero, V. Ice-nucleating and antifreeze proteins recognize ice through a diversity of anchored clathrate and icelike motifs. *J. Am. Chem. Soc.* 2018, 140, 4905-4912.; Nutt, D. R.; Smith, J. C. Dual function of the hydration layer around an antifreeze protein revealed by atomistic molecular dynamics simulations. *J. Am. Chem. Soc.* 2008, 130, 13066-13073.). As such, AF(G)P can bind to a specific plane of an ice crystal, while the inventive AF(G)P-conjugated Au NCs can bind to all the ice crystal planes, resulting from the randomness of the spatial arrangement of (Thr)$_5$-Cys. This nonspecific binding of the inventive AF(G)P-conjugated Au NCs can be confirmed by the absence of dynamic ice shaping (DIS) under the equilibrium-like directional growth of a single crystalline ice. The interfacial line (i.e., freezing front in FIG. 11*e*) between the growing ice and water was evenly grown from the supercooled place to ambient temperature area. In contrast, adding of zirconium acetate (ZrAc), known to bind to a specific plane of ice (i.e., prism plane), selectively inhibited the growth of corresponding ice crystal plane, in that a saw-tooth-like morphology, resulting from DIS, was clearly observed at the boundary between the growing ice and water (FIGS. 15*a* and *b*). A sucrose assisted DIS assay provided evidence of the absence of DIS in the AF(G)P-conjugated Au NCs according to the present invention (FIG. 15C). Because the sharp protrusions of growing ice, originating from DIS, may readily rupture cells or tissues (Ishiguro, H.; Rubinsky, B. Mechanical interactions between ice crystals and red blood cells during directional solidification. *Cryobiology* 1994, 31, 483-500.; Wang, J. H. A comprehensive evaluation of the effects and mechanisms of antifreeze proteins during low temperature preservation. *Cryobiology* 2000, 41, 1-9.), omnidirectional inhibition of ice growth could be advantageous in terms of practical biomedical applications using cryoprotectants.

Figure 16B:
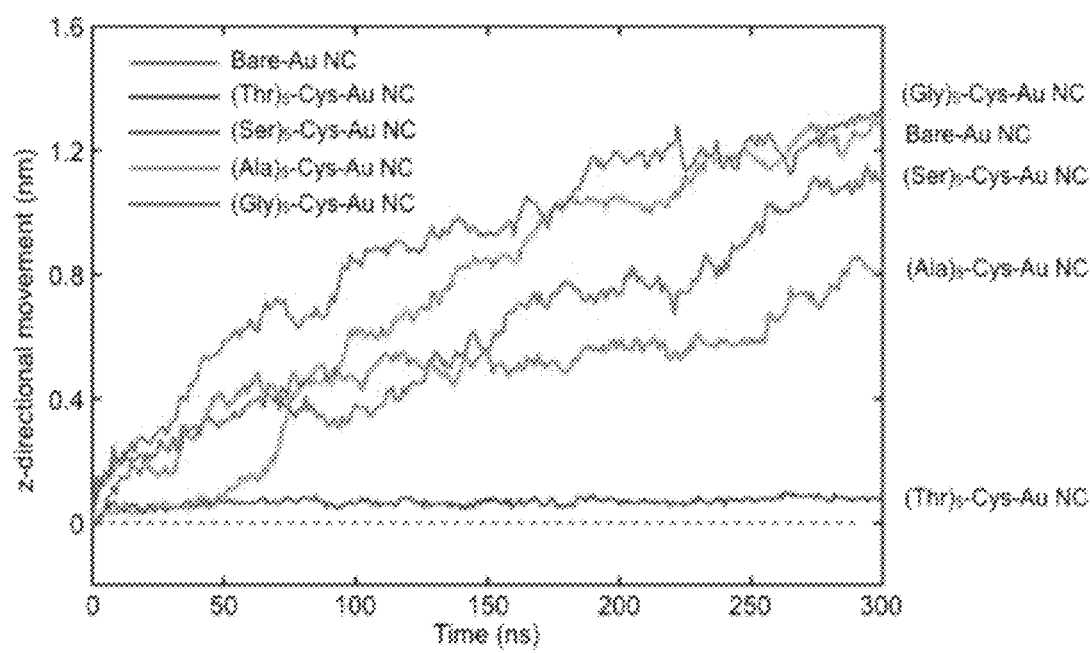
FIG. 16B is a graph showing a time-traced z-directional movement of bare Au NC, and $(Thr)_5$-Cys-, $(Ser)_5$-Cys-, $(Ala)_5$-Cys-, and $(Gly)_5$-Cys-conjugated Au NCs during ice growth.

Such an improved interfacial interaction between oligopeptide-conjugated Au NCs and the growing ice was theoretically confirmed using MD simulations. An AA simulation was used to reflect the realistic experimental condition in FIG. 11. A continual ice growth system, in which ice grow from the bottom to the top as shown in FIG. 16A, was constructed. The Au NCs were set to be placed on a secondary prism plane of the growing ice crystals, which is known as the fastest growing face (1 1 2 0). An appropriate space (1 nm) between the growing ice crystals and Au NCs allowed the ice-seeding effect to be minimized while simultaneously inducing free contact. To mimic the inventive oligopeptide-conjugated Au NCs, oligopeptides with a sequence of (Thr)$_5$-Cys, (Ser)$_5$-Cys, (Ala)$_5$-Cys, and (Gly)$_5$-Cys were set to be randomly attached to the Au NCs. Both bare Au NCs and oligopeptide-conjugated Au NCs were individually traced during continual ice growth for 300 ns at 268 K.

Figure 17A:
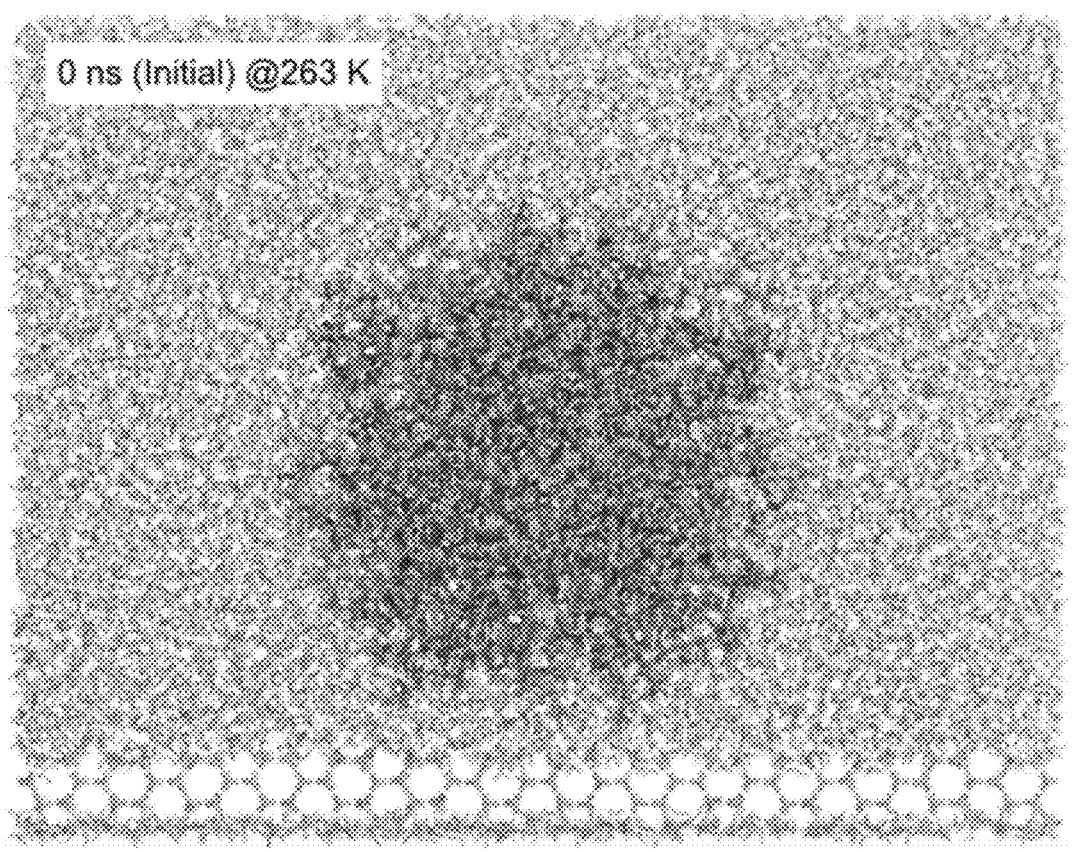
FIG. 17 is photographs showing shapes of $(Thr)_5$-Cys-conjugated Au NCs at start time (0 s) (FIG. 17A) and end time (300 ns) (FIG. 17B) during all atom molecular dynamics (AA MD) simulation.
Figure 17B:
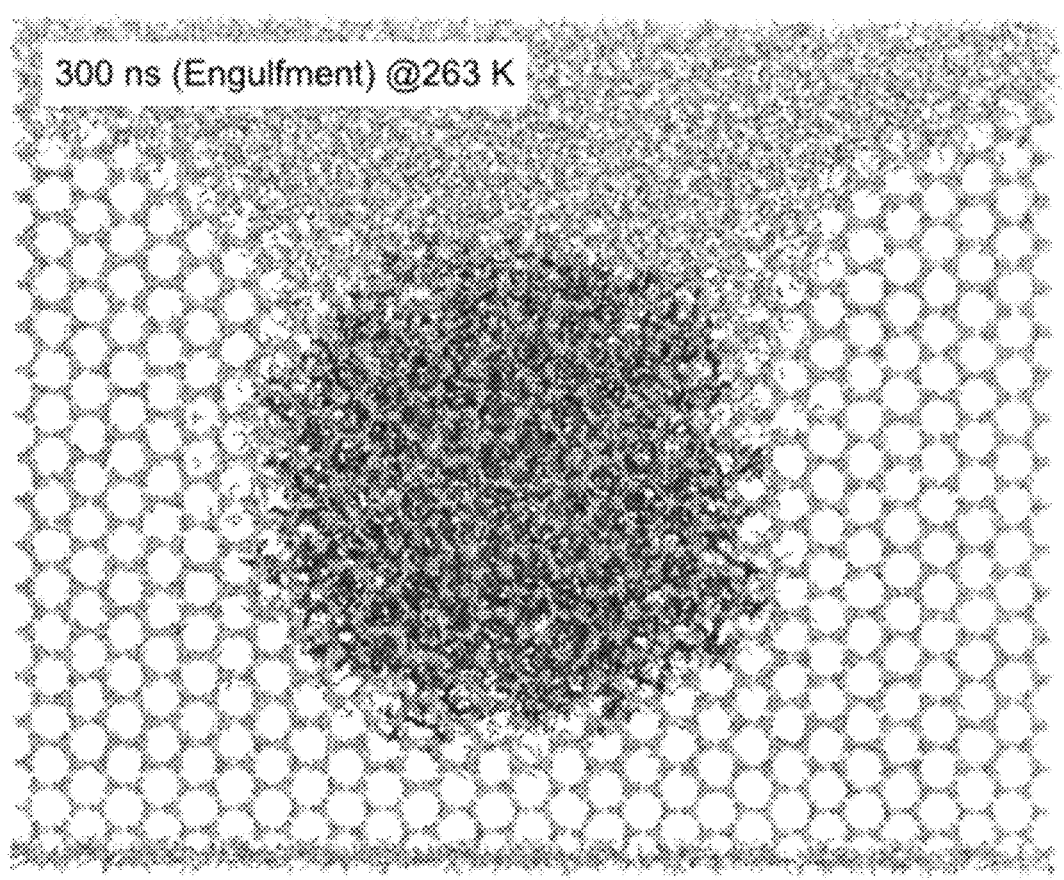
Figure 18A:
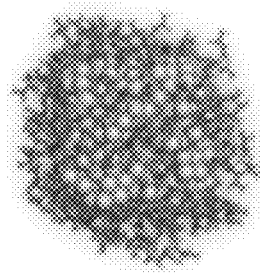
FIG. 18A is photographs showing the AA MD model for $(Thr)_n$-Cys-conjugated Au NCs with various densities.
Figure 18A:
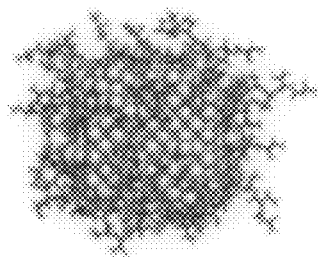
Figure 18A:
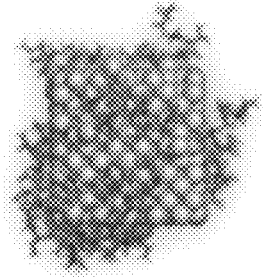
Figure 18A:
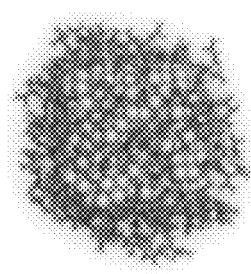
Figure 18A:
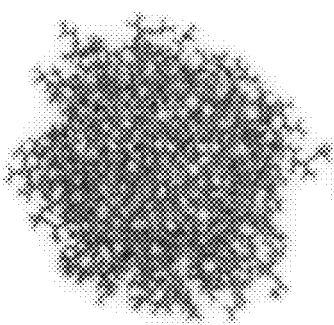
Figure 18A:
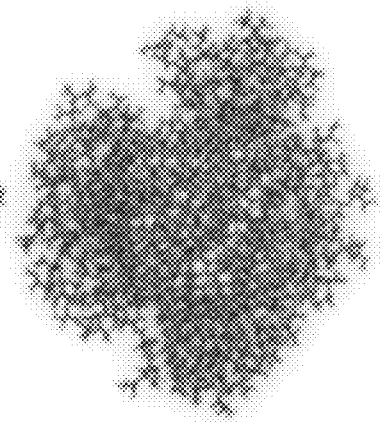
Figure 18B:
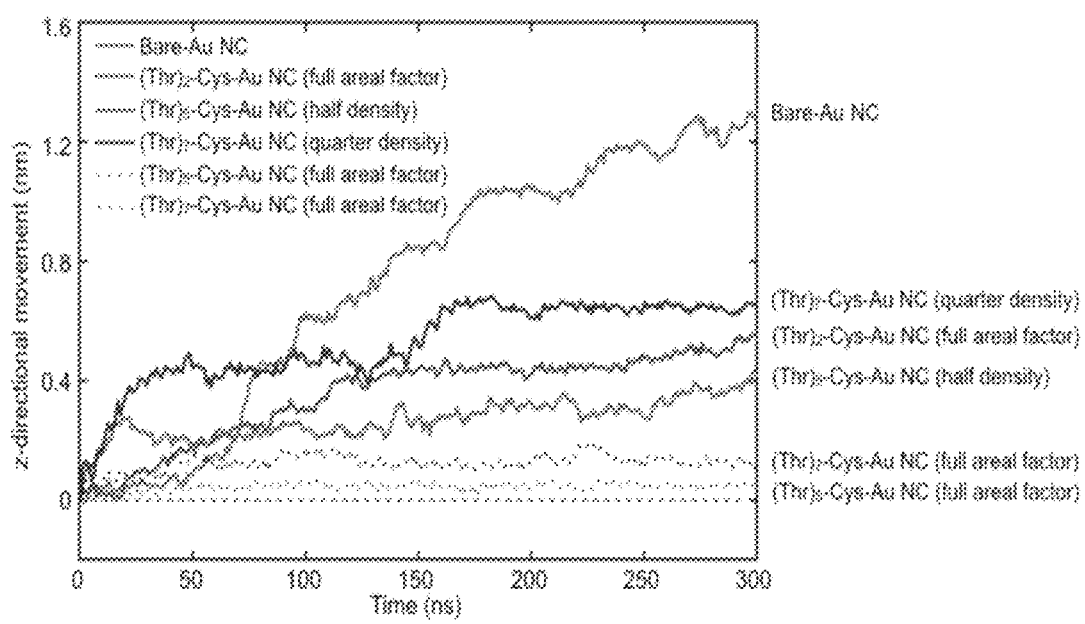
FIG. 18B is a graph showing a time-traced z-directional movement of $(Thr)_n$-Cys-conjugated Au NCs with various n and oligopeptide densities.

Similar to the experimental results, the bare Au NCs were continuously pushed up by the growing ice crystals, whereas the oligopeptide-conjugated Au NCs were directly adsorbed onto the ice crystals and thoroughly inhibited ice growth (FIG. 16A). As such, the growing ice plane, inhibited by the direct adsorption of (Thr)$_5$-Cys-conjugated Au NCs, become more curved, such that the Kelvin effect was induced. However, other oligopeptide-conjugated Au NCs adsorb less onto the growing ice crystal at 268 K, such that the flat freezing front was maintained without significant curvature during the ice growth. Indeed, the z-directional movement of (Thr)$_5$-Cys-conjugated Au NCs remained almost intact (displacement of 0.04 nm for 300 ns), which was in significant contrast with the considerable displacement of the bare Au NCs (displacement of 1.2 nm for 300 ns) or (Ser)$_5$-Cys/(Gly)$_5$-Cys-conjugated Au NCs (displacement of 1.0 to 1.2 for 300 ns). Meanwhile, (Ala)$_5$-Cys-conjugated Au NCs exhibited a moderate displacement of 0.8 nm for 300 ns. These predictions from MD simulations matched well with the IRI experiment results (FIG. 6). It is noteworthy that a full engulfment of (Thr)$_5$-Cys-conjugated Au NCs within the growing ice occurred by further reducing the temperature from 268 K to 263 K (FIG. 17).

Figure 16C:
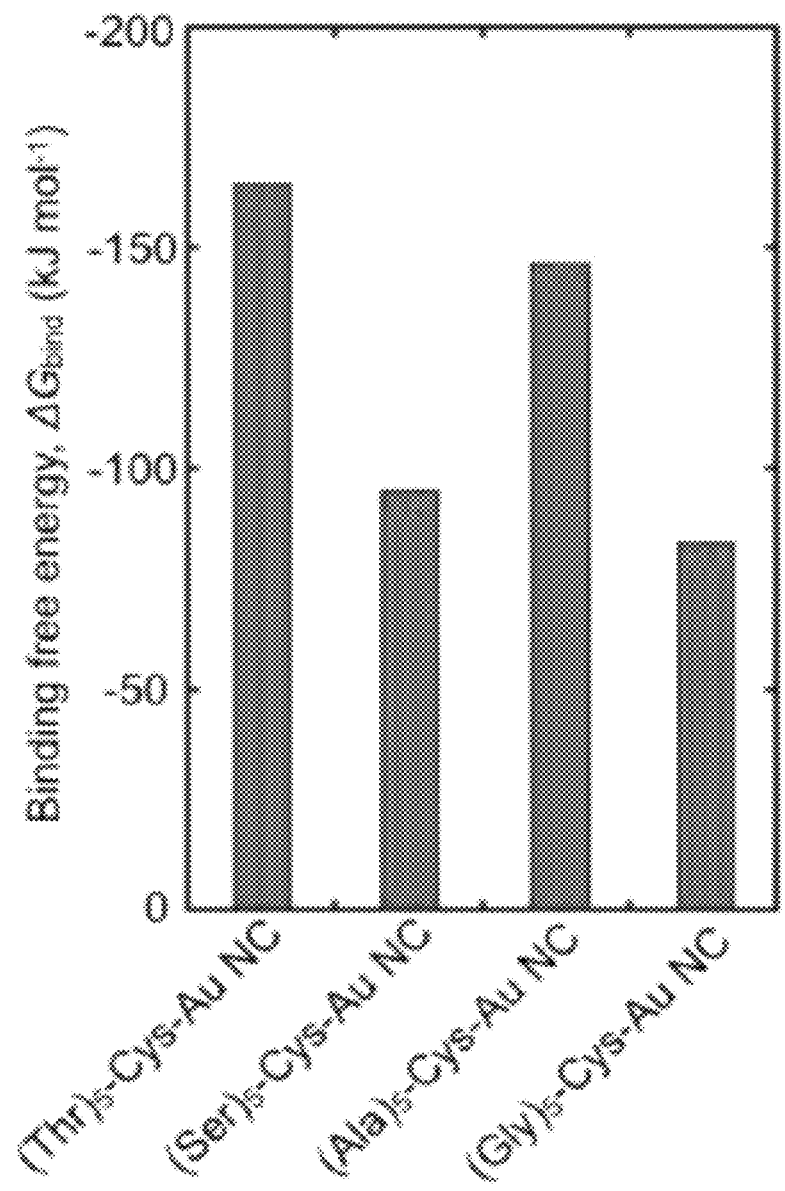
FIG. 16C is a graph showing a change in the calculated free energy of the oligopeptide-conjugated Au NCs obtained from an umbrella sampling simulation.
Figure 16D:
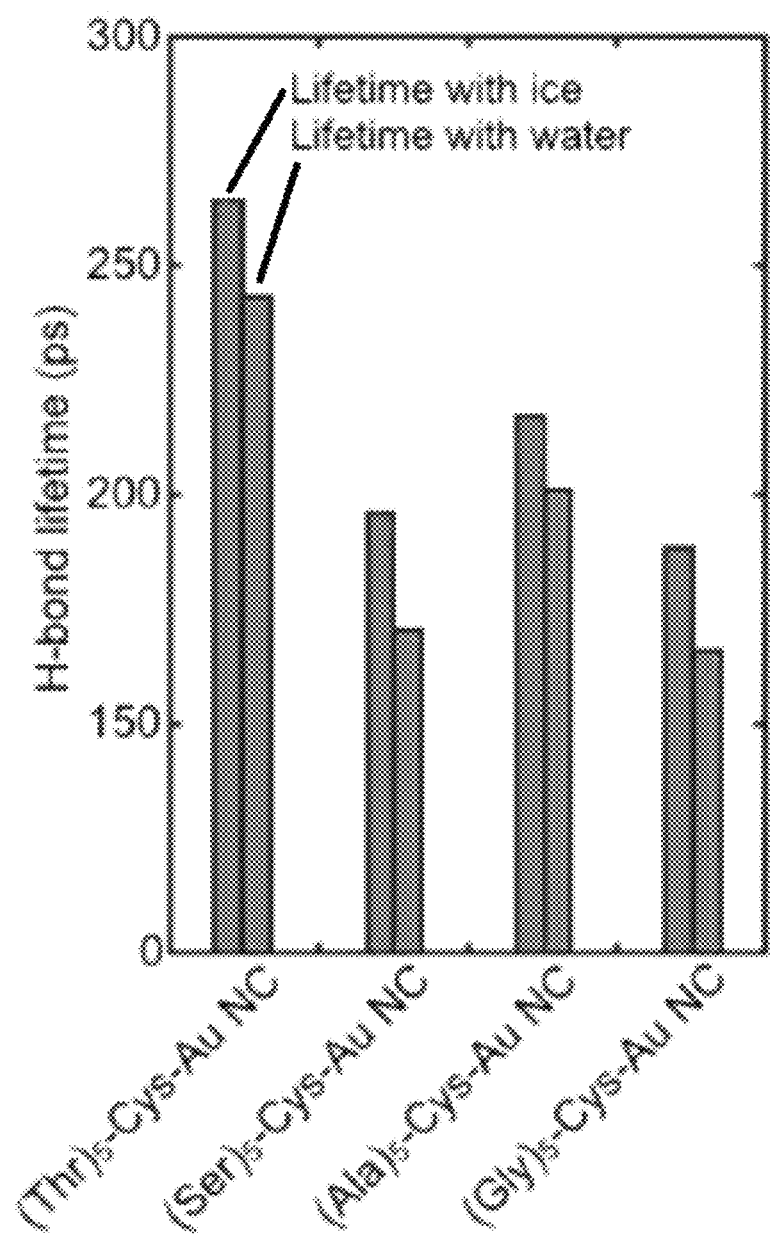
FIG. 16D is a graph showing the calculated results of hydrogen bonding lifetime of the oligopeptide-conjugated Au NCs.

Furthermore, free energy variations ($\Delta G_{bind}$) and hydrogen-bonding lifetime during binding between the 5 mer-Thr/-Ser/-Ala/-Gly oligopeptide-conjugated Au NCs and ice water molecules were measured (FIGS. 16*c* and *d*). Similar to both experimental analyses on IRI/ice affinity and theoretical analyses on z-directional movement, Thr assemblies on the Au NCs exhibited the largest reduction in the free energy and the longest hydrogen-bonding lifetime during their adsorption onto the growing ice crystals: wherein $\Delta G_{bind}$ and hydrogen bonding lifetimes were in the order of Thr, Ala, Ser, and Gly. Once again, it has been confirmed that the growth of ice was synergistically inhibited by the direct adsorption of oligopeptide-conjugated Au NCs onto the growing ice, due to the interaction of the hydrogen bonding and hydrophobic groups.

Through the MD simulations, the effect of n on IRI in terms of z-directional movement was also investigated (FIG. 18). Once the surface density of oligopeptides attached onto the Au NCs was fixed, (Thr)$_5$-Cys outperformed both (Thr)$_2$-Cys and (Thr)$_7$-Cys. In addition, half the number of (Thr)$_5$-Cys exhibited better performance than the case of full number. These results are fully consistent with the experimental results.

2.3 Effect of Au Colloidal Shapes on IRI Behavior

Figure 19A:
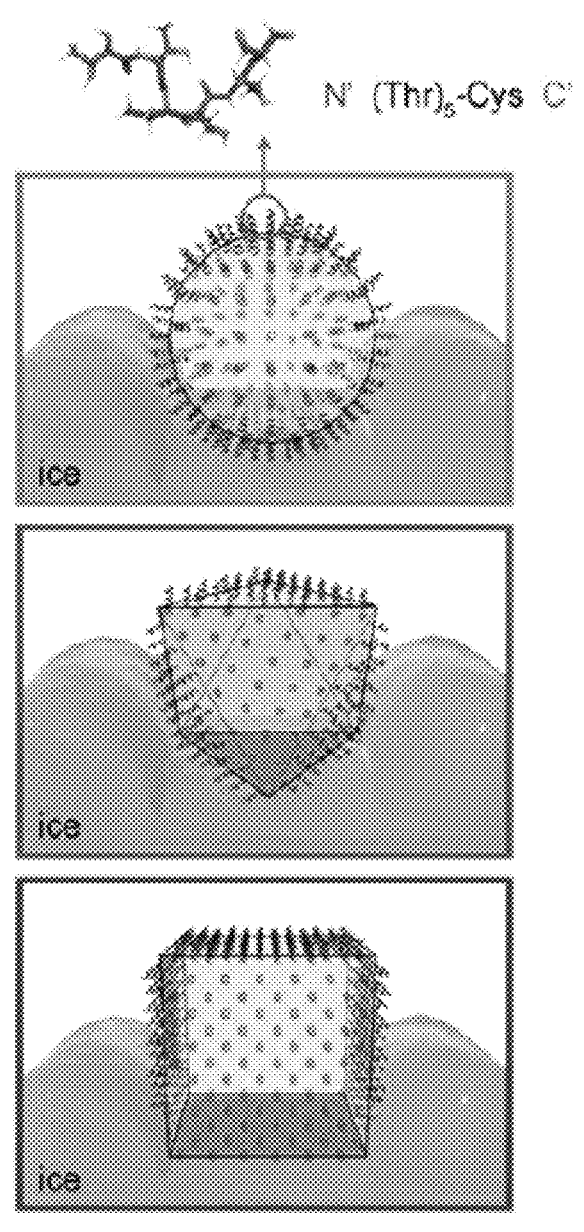
Figure 19B:
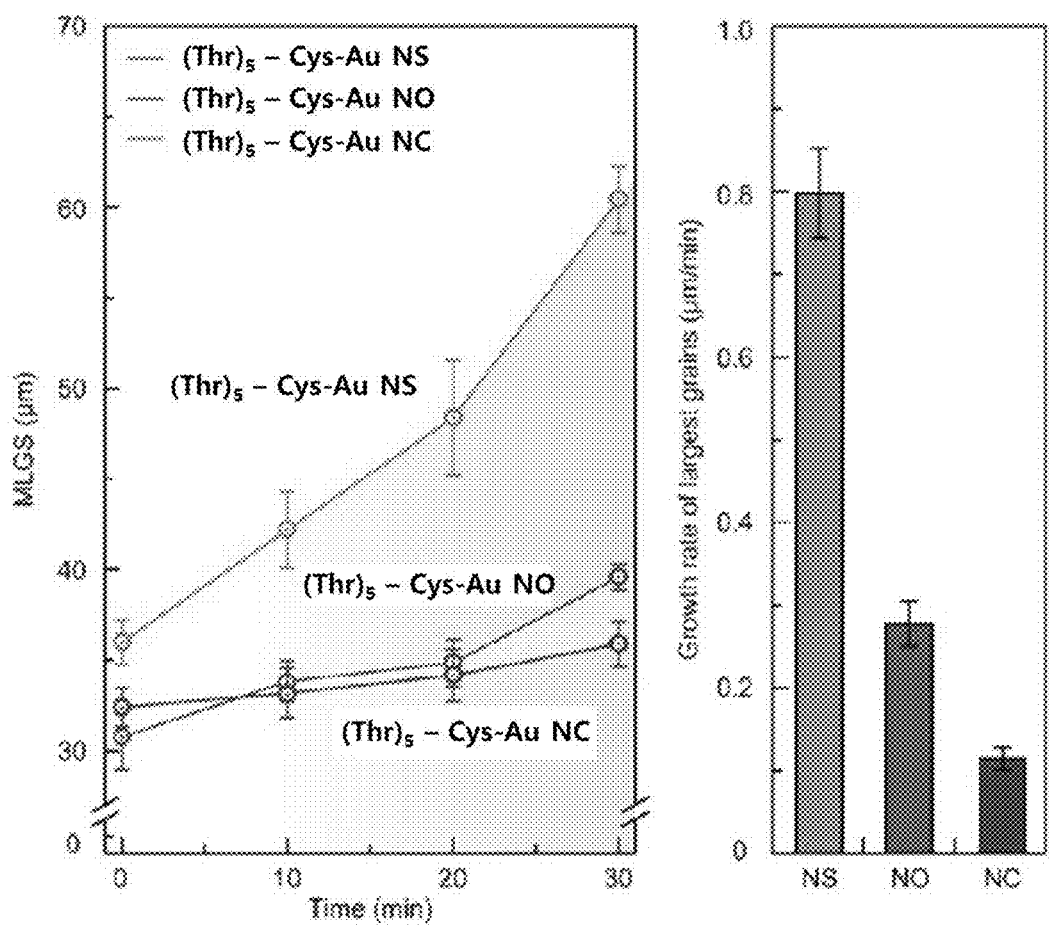
FIG. 19B is a diagram showing time-traced MLGS and growth rates of the largest grains of recrystallized ice for $(Thr)_5$-Cys-conjugated Au nanospheres (NSs), nanooctahedra (NOs), and nanocubes (NCs)
Figure 19C:
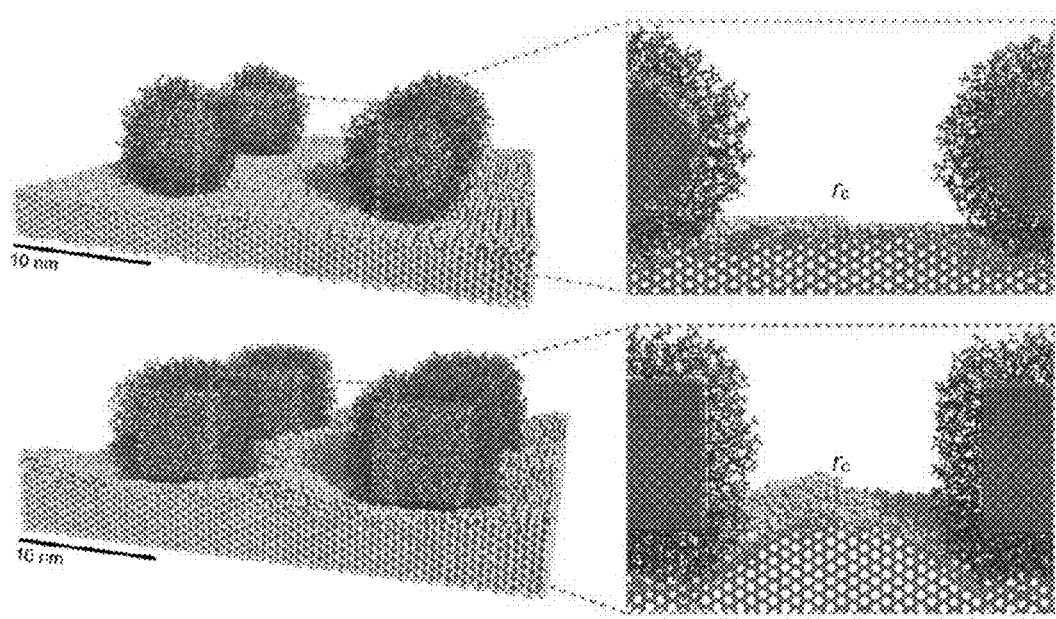
FIG. 19C is a photographs showing the simulated ice crystal growth with a regular array of $(Thr)_5$-Cys-conjugated Au NSs and NCs.

Effects of Au colloidal shapes on the IRI behavior were evaluated (FIG. 19). Due to the use of Au colloids with different shapes, the interfacial contact between growing ice and oligopeptide assemblies may be modulated (FIG. 19*a*). Herein, all the sizes of Au NSs, NOs, and NCs were equal to 75 nm; and the concentration across all the (Thr)$_5$-Cys-conjugated Au NPs was set to be 0.2 nM. As shown in FIG. 19*b*, the IRI effect was reduced in the order of Au NCs, NOs, and NSs. This experimental result implies that a facet contact may be advantageous the interacial interaction between growing ice and (Thr)$_5$-Cys-conjugated Au colloids, as compared to a point contact.

Figure 20A:
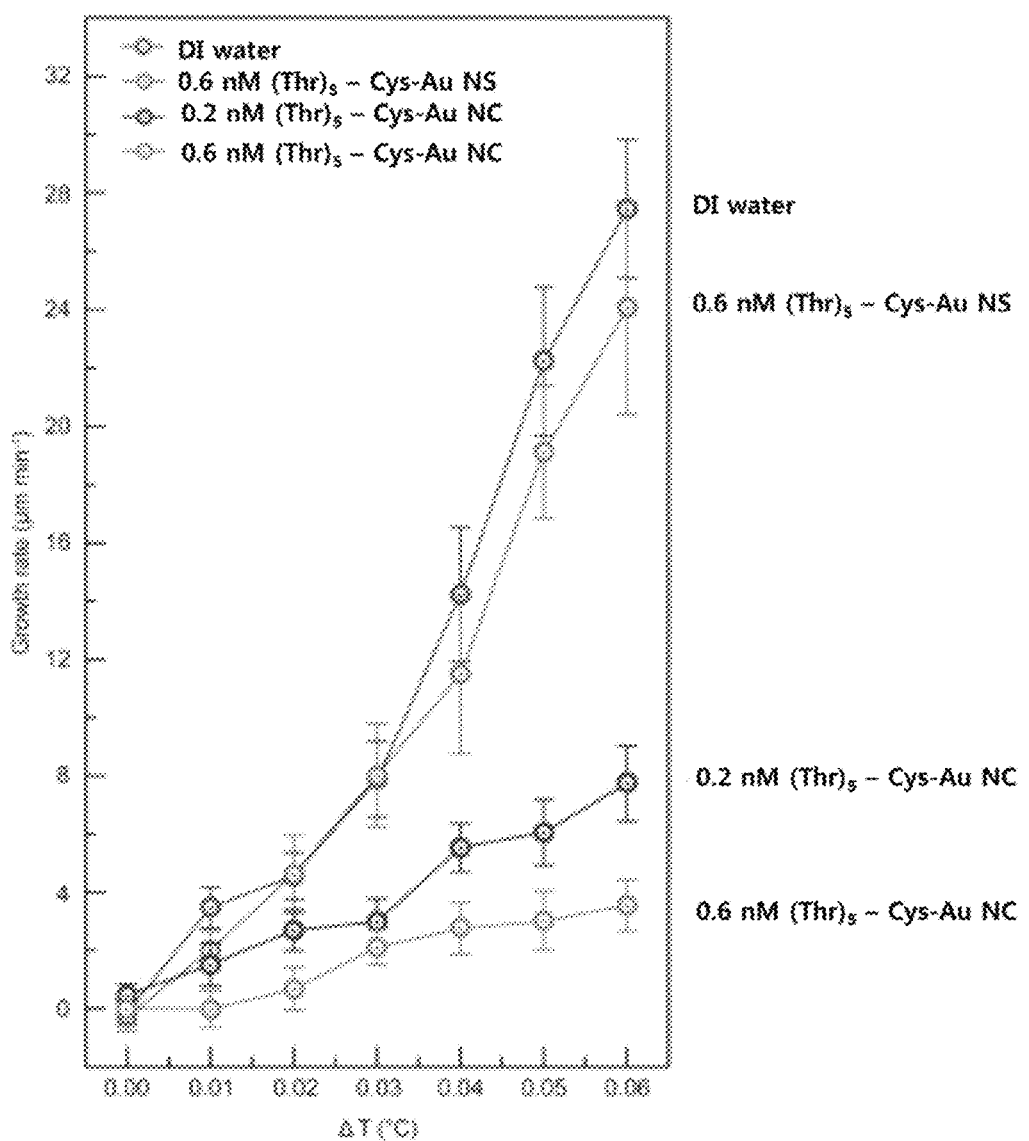
FIG. 20A is a graph showing growth rates of ice crystals at different supercooling temperatures under conditions of DI water, and 0.2 or 0.6 nM of $(Thr)_5$-Cys-conjugated Au NS suspension, and photographs.
Figure 20B:
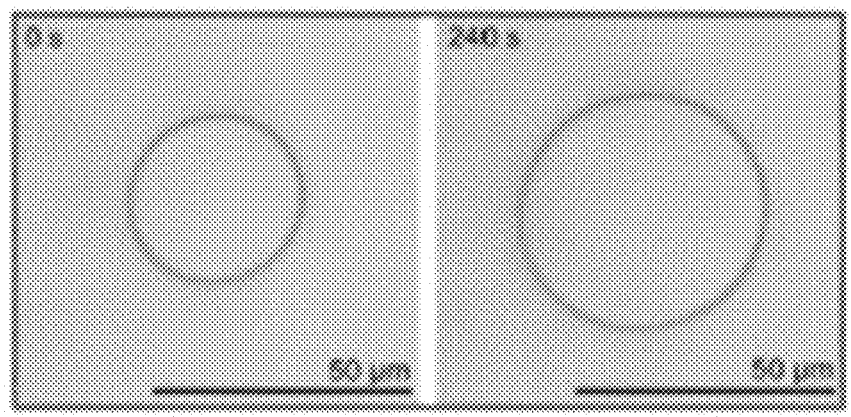
FIG. 20B is a graph showing time-lapse BFOM images of a single ice crystal under conditions of DI water, and 0.2 or 0.6 nM of $(Thr)_5$-Cys-conjugated Au NS suspension.
Figure 20B:
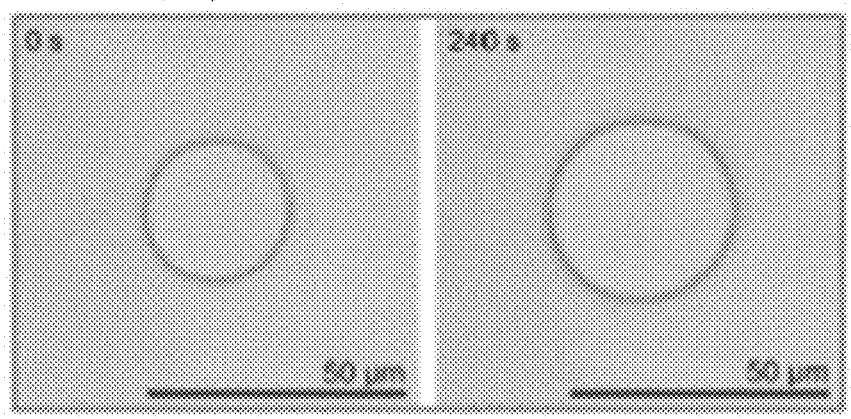
Figure 20B:
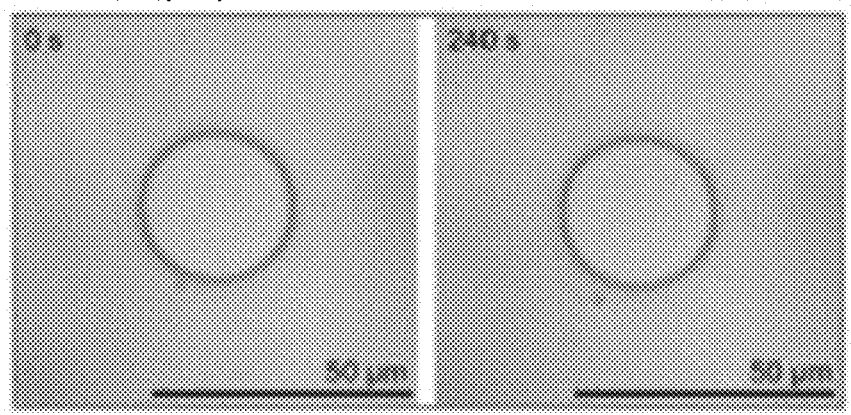

Such an effect of the Au colloidal shapes on IRI behavior was further verified through a large-scale AA MD simulation. Then, the inhibition of ice growth between the Au NSs and the Au NCs was compared (FIGS. 19*c* and *d*), both of which have (Thr)$_5$-Cys attached thereto. In this MD simulation, the Au NSs and the NCs were set to be regularly arrayed with the same spacing. During continual ice growth at 268 K for 100 ns, the radius of curvature of the growing ice between Au NCs was smaller than that between Au NSs. This phenomenon is mainly because the Au NCs can contact the growing ice crystals more conformably than the Au NSs. As such, the facet contact of Au NCs was indeed advantageous over the point contact of Au NSs by reducing the radius of curvature of the growing ice crystal, thereby leading to greater decrease in the freezing temperature due to the enhanced Kelvin effect. Actually, $(Thr)_5$-Cys-conjugated Au NCs beyond 0.6 nM started to induce a thermal hysteresis (TH) of 0.01° C., whereas Au NSs did not induce the same (FIG. 20A and FIG. 20B). Therefore, from the above-described results, it can be seen that the shape of colloidal cryoprotectants plays a key role in boosting the IRI effect.

For the purposes of the claims, the claims described below should not be interpreted in any way as narrower than its literal language, and therefore the illustrative embodiment from the specification should not be read as the claims. Accordingly, it should be understood that the present invention has been described by way of example and is not intended to limit the scope of the claims. Therefore, the present invention is limited only by the following claims. The entireties of all publications, published patents, patent applications, books and journal articles cited in the present application are incorporated by reference herein.

What is claimed is:

1. A nanostructure comprising:
    a core comprising one or more planes configured to come into planar contact with at least one plane of an ice crystal; and
    an oligopeptide which is conjugated to at least one plane of the core and comprises $(Thr)_n$-, $(Ala)_n$-, $(Ser)_n$-, or $(Gly)_n$-,
    wherein the core has a polyhedron shape, and the nanostructure is a polyhedron-shaped nanostructure present in water in a colloidal form to control freezing, and
    n is an integer of 2 to 7,
    wherein the nanostructure has a higher ice recrystallization inhibition (IRI) activity than the same nanostructure but in a sphere-shaped structure.

2. The nanostructure according to claim 1, wherein the polyhedron shape comprises tetrahedron, truncated tetrahedron, hexahedron, truncated hexahedron, octahedron, truncated octahedron, decahedron, dodecahedron, icosahedron, tetrakishexahedron, hexakisoctahedron, or rhombic dodecahedron.

3. The nanostructure according to claim 1, wherein the core is made of gold (Au), silver (Ag), platinum (Pt), palladium (Pd), aluminum (Al), copper (Cu), iron oxide ($Fe_3O_4$), or silicon dioxide ($SiO_2$), or an alloy including at least two thereof.

4. The nanostructure according to claim 1, wherein the core is made of gold (Au), platinum (Pt), iron (Fe), iron oxide ($Fe_3O_4$), silicon (Si), or silicon dioxide ($SiO_2$), or an alloy including at least two thereof.

5. The nanostructure according to claim 1, wherein n is 3 to 6.

6. The nanostructure according to claim 1, wherein the oligopeptide comprises $(Thr)_n$-, or $(Ala)_n$-.

7. The nanostructure according to claim 1, wherein the core has a diameter of 50 nm to 100 nm.

8. The nanostructure according to claim 1, wherein 0.07 to 0.25 oligopeptides per $nm^2$ are attached to the plane.

9. The nanostructure according to claim 1, wherein the core has a shape of a hexahedron or octahedron.

10. The nanostructure according to claim 1, wherein the core is made of gold (Au).

11. The nanostructure according to claim 1, wherein n is 5.

12. The nanostructure according to claim 1, wherein 0.1 to 0.2 oligopeptides per $nm^2$ are attached to the plane.

13. The nanostructure according to claim 1, wherein the freezing control is performed by inhibiting recrystallization of the ice.

14. A composition for controlling freezing comprising the nanostructure according to claim 1.

15. A composition for freezing a cell comprising the nanostructure according to claim 1.

16. A composition for freezing a food comprising the nanostructure according to claim 1.

17. A method for cryopreserving a cell comprising: adding the nanostructure according to claim 1, to a solution containing the cells.

18. A method for cryopreserving a food comprising: adding the nanostructure according to claim 1, to the food for treatment.

* * * * *